US008618264B2

(12) United States Patent
Cunningham et al.

(10) Patent No.: US 8,618,264 B2
(45) Date of Patent: Dec. 31, 2013

(54) ANTI-CD147 ANTIBODIES, METHODS AND USES

(75) Inventors: Mark Cunningham, Radnor, PA (US); Bethany Swencki-Underwood, Radnor, PA (US); Yi Tang, Radnor, PA (US); Li Yan, Berwyn, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 112 days.

(21) Appl. No.: 13/062,702

(22) PCT Filed: Aug. 19, 2009

(86) PCT No.: PCT/US2009/054289
§ 371 (c)(1),
(2), (4) Date: Mar. 8, 2011

(87) PCT Pub. No.: WO2010/036460
PCT Pub. Date: Apr. 1, 2010

(65) Prior Publication Data
US 2011/0200627 A1 Aug. 18, 2011

Related U.S. Application Data

(60) Provisional application No. 61/100,848, filed on Sep. 29, 2008.

(51) Int. Cl.
*C07K 16/30* (2006.01)
(52) U.S. Cl.
USPC .................. 530/388.8; 530/387.3; 530/388.1
(58) Field of Classification Search
None
See application file for complete search history.

(56) References Cited

U.S. PATENT DOCUMENTS

| 5,330,896 | A | 7/1994 | Billing |
| 5,643,740 | A | 7/1997 | Billing et al. |
| 8,338,573 | B2 * | 12/2012 | Chen et al. .................. 530/387.1 |
| 2005/0026841 | A1 | 2/2005 | Chen et al. |
| 2005/0176933 | A1 | 8/2005 | Chen et al. |
| 2005/0214302 | A1 | 9/2005 | Nakada et al. |
| 2006/0258852 | A1 | 11/2006 | Lugovskoy et al. |
| 2007/0048305 | A1 | 3/2007 | Davis et al. |
| 2007/0048315 | A1 | 3/2007 | Presta |
| 2007/0178098 | A1 | 8/2007 | Way et al. |
| 2008/0008719 | A1 | 1/2008 | Bowdish et al. |
| 2008/0050375 | A1 | 2/2008 | Davies et al. |
| 2008/0131912 | A1 | 6/2008 | Tu et al. |
| 2011/0200627 | A1 | 8/2011 | Cunningham et al. |

FOREIGN PATENT DOCUMENTS

| CN | 101139391 A | 3/2008 |
| WO | WO 2006/039343 A2 | 4/2006 |

OTHER PUBLICATIONS

Paul, Fundamental Immunology, 3rd Edition, 1993, pp. 292-295.*
Tsurushita et al., Methods, 2005; 36:69-83.*
Dall'Acqua et al., Methods 2005; 36:43-60.*
Bao et al., "Isolating human antibody against human hepatocellular carcinoma by guided-selection", Cancer Biology & Therapy 2005, 4 (12): 1374-1380.
Uniprot-submission Q9QXE9, Jun. 10, 2008 Retrieved from the Internet: <URL:www.uniprot.org/uniprot/Q9QXE9.txt?version=33>.
Yan et al., "Roles of the multifunctional glycoprotein, emmprin (basigin; CD147), in tumour progression", Throm Haemost, 2005, 93(2):199-204.
International Search Report for PCT/US09/54289 dated May 15, 2012.
Miyauchi et al., "The Basigin Group of the Immunoglobulin Superfamily: Complete Conversion of a Segment in and around Transmembrane Domains of Human and Mouse Basiginand Chicken HT7 Antigen", Journal Biochem. (Tokyo) vol. 110, pp. 770-774 (1991).
Kanekura et al., "Basigin, a New Member of the Immunoglobulin Superfamily: Genes in Different Mammalian Specia, Glycosylation Changes in the Molecule from Adult Organs and Possible Variation in the N-terminal Sequences", Cell Structure and Function, vol. 16, pp. 23-30 (1991).
Billings et al., "Monoclonal and Heteroantibody Reacting with Different Antigens Common to Human Blast Cells and Monocytes" Hybridoma, vol. 1, pp. 303-311 (1982).
Heslop et al., "Response of steroid-resistant graft-versus-host disease to lymphoblast antibody CBL1", The Lancet, vol. 346, pp. 805-806 (1995).
Deeg et al., "Treatment of steroid-refractory acute graft-versus-host disease with anti-CD 147 monoclonal antibody ABX-CBL", Blood, vol. 98, pp. 2502-2058 (2001).
Koch et al., T cell activation-associated epitopes of CD147 in regulation of the T cell response, and their definition by antibody affinity and antigen density, International Immunology, vol. 11(5), pp. 777-786 (1999).
Ellis, "Monoclonal Antibody Preparation and Purification of a Tumor Cell Collagenase-stimulatory Factor", Cancer Research, vol. 49, pp. 3385-3391 (1989).
Biswas et al., "The Human Tumor Cell-derived Collagenase Stimulatory Factor (Renamed EMMPRIN) Is a Member of the Immunoglobulin Superfamily", Cancer Research, vol. 55, pp. 434-439 (1995).

(Continued)

*Primary Examiner* — Sheela J Huff
*Assistant Examiner* — Jessica H Roark
(74) *Attorney, Agent, or Firm* — Kenneth J. Dow

(57) ABSTRACT

The present invention provides antibodies immunospecific for human CD147 capable of blocking bioactivity of CD147 associated with malignant disease such as the stimulation of MMPs from fibroblast cells by tumor cells, the release of VEGF, and the promotion of angiogenesis. The antibodies of the present invention of are useful in treating malignant disease and those diseases in which CD147 activity is plays a pathogenic role, such as diseases of the eye, lung, and cardiovascular system.

5 Claims, 13 Drawing Sheets

(56) References Cited

OTHER PUBLICATIONS

Ku et al., "Epitope Mapping of Series of Monoclonal Antibodies Against the Hepatocellular Carcinoma-associated Antigen HAb18G/CD147", Scand. J. Immunol, vol. 65(5), pp. 435-443 (2007).
Berditchevski et a., "Generation of Monoclonal Antibodies to Integrin-associated Proteins", The Journal of Biological Chemistry, vol. 272, No. 46, pp. 29174-29180 (1997).
Chiampanichayakul et al., "CD147 contains different bioactive epitopes involving the regulation of cell adhesion and lymphocyte activation", Immunobiology, vol. 211, pp. 167-178 (2006).
Renno et al., "A role for CD147 in Thymic Development", The Journal of Immunology, vol. 168, pp. 4946-4950 (2002).
Tang et al., "Extracellular Matrix Metalloproteinase Inducer Stimulates Tumor Angiogenesis by Elevating Vascular Endothelial Cell Growth Factor and Matrix Metalloproteinases", Cancer Research, vol. 65 (8), pp. 3193-3199 (2005).
Xu et al., "A Randomized Controlled Trial of Licartin for Preventing Hepatoma Recurrence After Liver Transplantation", Hepatology, vol. 45, pp. 269-275 (2007).
Wang, Li et al., "Regulation of matrix metalloproteinase production and tumour cell invasion by four monoclonal antibodies against different epitopes of HAb18G/CD147 extracellular domain", *Hybridoma* vol. 25, pp. 60-67, XP009168160, Jan. 2006.
Jing, Xu et al., "HAb18G/CD147 functions in invasion and metastasis of hepatocellular carcinoma", *Molecular Cancer Research* vol. 5, No. 6, pp. 605-614, XP002694055, Jun. 2007.
Janssen Biotech, Inc., Supplemental Extended European Search Report dated Apr. 15, 2013 for EP 09 81 6663.
Hui Ye et al., "Preparation of functional characterization of the monoclonal antibody HAb18Gedomab1", World Chinese Journal of Digestology, vol. 12, No. 9, pp. 2061-2065 (Sep. 15, 2004).
Janssen Biotech, Inc., Chinese Office Action dated Aug. 5, 2013 for CN 2009801392778.4.

\* cited by examiner

Fig. 1

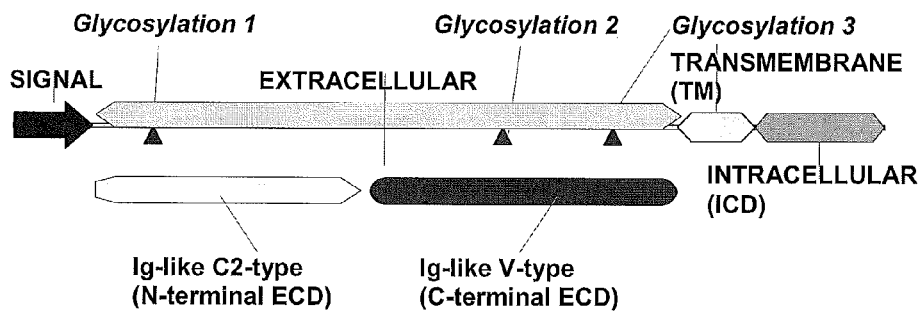

```
                              Ig-like C2-type (N-terminal ECD)
                              ~~~~~~~~~~~~~~~~~~~~~~~~~~~~~~
                   Signal
                   ~~~~~~~~~~~~~~~~~~~~~~~~
(SEQ ID NO:1)   1  MAAALFVLLG FALLGTHGAS GAAGTVFTTV EDLGSKILLT CSLNDSATEV
                     Ig-like C2-type (N-terminal ECD)
                   ~~~~~~~~~~~~~~~~~~~~~~~~~~~~~~~~~~~~~~~~~~~~~~~~~~
(SEQ ID NO:1)  51  TGHRWLKGGV VLKEDALPGQ KTEFKVDSDD QWGEYSCVFL PEPMGTANIQ
                   Ig-like C2-type (N-terminal ECD)
                   ~~~
                             Ig-like V-type (C-terminal ECD)
                             ~~~~~~~~~~~~~~~~~~~~~~~~~~~~~~~~~~~~~~~
(SEQ ID NO:1) 101  LHGPPRVKAV KSSEHINEGE TAMLVCKSES VPPVTDWAWY KITDSEDKAL
                        Ig-like V-type (C-terminal ECD)
                   ~~~~~~~~~~~~~~~~~~~~~~~~~~~~~~~~~~~~~~~~~~~~~~~~~
(SEQ ID NO:1) 151  MNGSESRFFV SSSQGRSELH IENLNMEADP GQYRCNGTSS KGSDQAIITL
                                                        Intracellular (ICD)
                                                        ~~~~~~~~~~~~~~~~~~~~
                        Transmembrane (TM)
                        ~~~~~~~~~~~~~~~~~~~~~~~~~
(SEQ ID NO:1) 201  RVRSHLAALW PFLGIVAEVL VLVTIIFIYE KRRKPEDVLD DDDAGSAPLK
                     Intracellular (ICD)
                   ~~~~~~~~~~~~~~~~~~~~~
(SEQ ID NO:1) 251  SSGQHQNDKG KNVRQRNSS
```

Fig. 4
A.
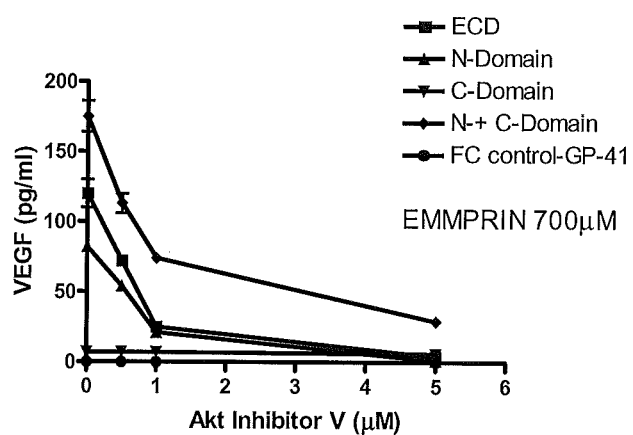
B.
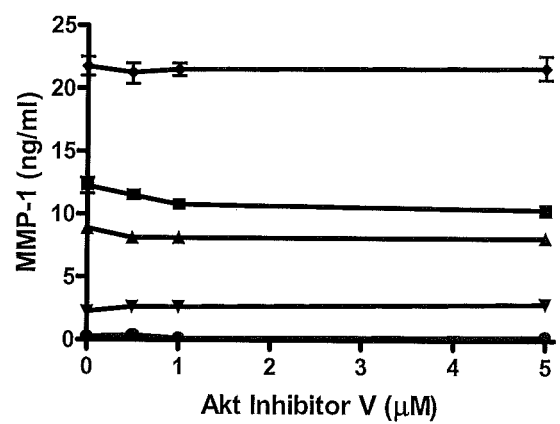

Fig. 5
A.
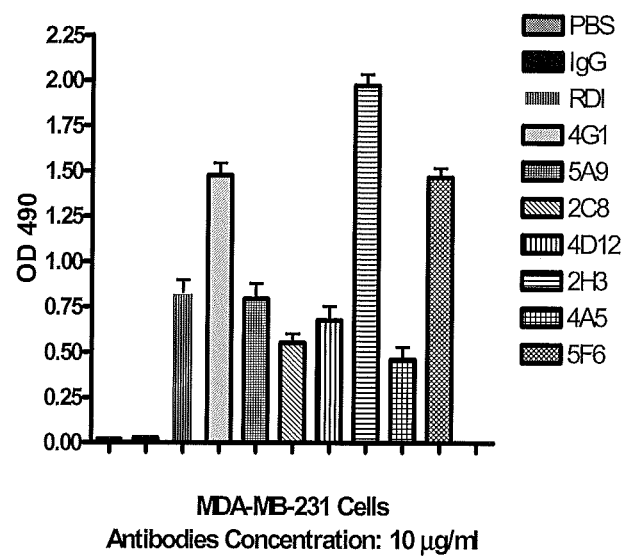
B.
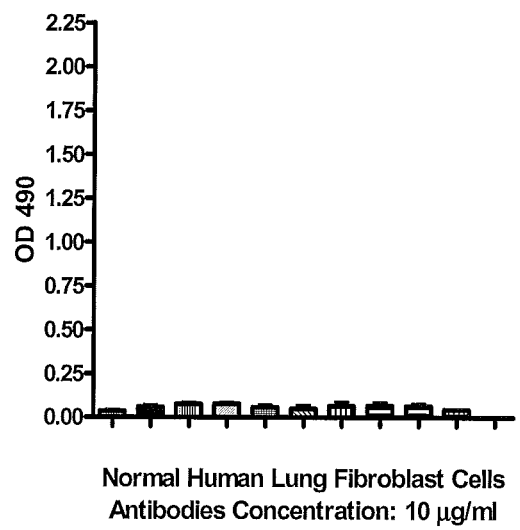

Fig. 12
H/D exchange perturbation of CD147 residues 19-117 by 4A5
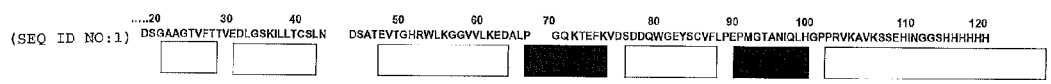
H/D exchange perturbation of CD147 residues 19-117 by 5F6
■ strongly H/D exchange protected by antibody
▨ weakly H/Exchange protected by antibody
☐ not protected
D45, G69 and Q70 identified by single point mutagenesis

ANTI-CD147 ANTIBODIES, METHODS AND USES

CROSS-REFERENCE TO RELATED APPLICATIONS

This application claims the benefit of International Application Number PCT/US2009/054289, filed 19 Aug. 2009, which claims the benefit of U.S. Provisional Application No. 61/100,848, filed 29 Sep. 2008. The entire contents of each of the aforesaid applications are incorporated herein by reference in their entirety.

BACKGROUND OF THE INVENTION

1. Field of the Invention

The present invention relates to anti-CD147 antibodies and their use as therapeutics.

2. Related Art

CD147 is a member of the immunoglobulin (Ig) superfamily that is expressed on a large number of different cells in a variety of tissues. It was originally named human Basigin (for basic immunogloblin superfamily) and was first cloned in about 1991. (Miyauchi et al. J Biochem (Tokyo) 110:770-774 (1991); Kanekura et al. Cell. Struct Funct 16:23-30 (1991); Miyauchi et al. J Biochem (Tokyo) 110:770-774 (1991)). The bsg gene product, CD147, also known as EMMPRIN (Extracellular Matrix Metalloprotein Inducer") isoform II (NCBI Accession No. NP_940991) is a propolypeptide 269 amino acids in length (SEQ ID NO: 1, FIG. 1), having a signal peptide 22 or 24 amino acids in length, a 183 amino acid extracellular domain, a transmembrane domain from residues 208-228, and an intracellular domain from residue 229 to the $269^{th}$ residue. According to the curated NCBI record, the extracellular domain (ECD) is comprised of two immunoglobulin-like domains: a C2-type domain from residue 22 to 103 and a V-like domain from residue 105-199 (FIG. 1). A number of splice variants have also been reported.

CD147 is a pleiotropic molecule playing a role in fetal development, retinal function, and in T-cell maturation. It has been shown to be a cell-surface receptor for cyclophilins. It is expressed in areas of tissue remodeling: tumors, endometrium, placenta, skin and regions undergoing angiogenesis (See Iacono et al. 2007. Exp Mol. Path 83:283-295) and stimulates matrix metalloproteinases (MMPs) and VEGF production. CD147 is induced upon monocyte differentiation and is expressed in human atheroma (Major T C, Liang L, Lu X, Rosebury W, Bocan T M. 2002. Arterioscler Thromb Vasc Biol. 22: 1200-1207). It has been shown that CD147 promotes invasion and metastasis in different tumor types via the induction of matrix metalloproteinases (MMPs) and the urokinase-type plasminogen activator system by peritumoral stromal cells. CD147 is also involved in angiogenesis, anoikis resistance, lactate efflux, multidrug resistance, and cell proliferation in cancer cells. CD147 overexpression and/or function has been associated with other pathological processes such as inflammatory responses, pulmonary fibrosis, rheumatoid arthritis, lupus erythematosus, heart failure, Alzheimer's disease and the infectivity cycle of the human immunodeficiency virus and coronaviruses in lymphocytes. (see Ruiz et al, J. Biol. Chem., Vol. 283, (9), 5554-5566, 2008). In addition, cleavage of CD147 and shedding of CD147 fragments may be involved in CD147 regulation or release of active fragments (Egawa et al. 2006 J Biol Chem 281(49): 37576-85).

Anti-CD147 antibodies have been reported. A murine antibody IgM mAbs, CBL1 (Billings et al. Hybridoma 1:303-311, 1982, U.S. Pat. Nos. 5,330,896 and 5,643,740), was tested in steroid-refractory acute graft-versus-host disease (Heslop et al. The Lancet 346: 805-806; Deeg et al. 2001 Blood 98:2052-8). Human equivalent mAbs binding to epitopes overlapping that of CBL1 (aka ABX-CBL), near the transmembrane domain of the ECD were also developed (US2007048305A1). Koch et al. (Internat Immunol 11(5) 777-786, 1999) mapped CD147 epitopes associated with T- and B-cell activation, reporting that only the highest affinity monoclonal antibody (MEM-M6/6) of a group of antibodies made to CD147 was effective in preventing human T-cell activation and proliferation by the mAbs against CD3, OKT3. A murine antibody to tumor cell derived human CD147, EIIF4 (Ellis, 1989 Cancer Res 49:3385-91; Biswas et al. Cancer Research 55, 434-439, 1995), demonstrated the ability to block lung carcinoma CD147 induced collagenase (matrix metalloproteinase-1 or MMP-1) activity from human fibroblasts. Binding of EIIF4 antibody to CD147 was shown to be abolished when a mutant ECD missing the N-terminal Ig domain was prepared (Biswas, C. et al., Cancer Res 55, 434-439, 1995). Ku et al. (Scan J Immunol 65(5) 435-443, 2007) identified mAbs described as inhibitory for the CD147 associated MMP axis and, by using truncated CD147 sequences, identified key residues at the N-terminus ($^{22}$A to $^{50}$V—SEQ ID NO.: 1) for CD147 MMP induction activity.

Thus, while certain antibodies and other antagonists of CD147 are known, how the complex nature of the protein, including the two immunoglobulin domains, influences the myriad biological activities has not been thoroughly illucidated. Domain specific antagonists may prove to be useful therapeutic candidates for treating various of the pathologies associated with CD147 display and/or activation on various tissues. For example, therapeutic agents capable of blocking production MMPs or VEGF activity induced by CD147 could be advantageous in cancer therapy.

Accordingly, there is a need to provide human antibodies specific for human CD147 for use in therapy to diminish or eliminate symptoms of CD147-dependent diseases, as well as improvements over known antibodies or fragments thereof.

SUMMARY OF THE INVENTION

The present invention provides anti-CD147 monoclonal antibodies capable of blocking activities associated with one or more bioactivities associated with CD147 including but not limited to angiogenesis, VEGF production, matrix metalloproteinase production (MMP-1, MMP-2, and MMP-9), and which antibody has a specific binding site on human CD147.

One aspect of the invention is an isolated antibody reactive with human CD147 protein having the antigen binding ability of a monoclonal antibody having the amino acid sequences of the light chain complementarity determining regions (CDRs) as set forth in SEQ ID NOs: 9, 11, 13 and 15 and the amino acid sequences of the heavy chain CDRs as set forth in SEQ ID NOs: 10, 12, 14 and 16.

Another aspect of the invention is an isolated antibody reactive with a CD147 protein epitope located at residues 65-75 of SEQ ID NO: 1 of the CD147 protein.

Another aspect of the invention is an isolated antibody having heavy chain CDR1, CDR 2 and CDR3 (Hc-CDR1, Hc-CDR2 and Hc-CDR3) amino acid sequences selected from the sequences shown in SEQ ID NOs: 10, 12 and 14 respectively and a light chain CDR3 (Lc-CDR3) as shown in Formula (I):

Gln Gln Xaa$_1$ Tyr Ser Xaa$_2$ Pro Xaa$_3$Thr     (I)

wherein Xaa$_1$ is Tyr or Asp; Xaa$_2$ is Tyr or Ser; Xaa$_3$ is Phe or Tyr or absent; and Xaa$_4$ is Thr or Phe; and light chain CDR1 (Lc-CDR1) and light chain CDR2 (Lc-CDR2) amino acid sequences selected from the sequences as shown in SEQ ID NOs: 9 and 11, respectively.

Another aspect of the invention is an isolated antibody having Hc-CDR1, Hc-CDR2 and Hc-CDR3 amino acid sequences shown in SEQ ID NOs: 10 and Lc-CDR1 Lc-CDR2, and Lc-CDR3 amino acid sequences as shown in SEQ ID NOs: 9.

Another aspect of the invention is an isolated antibody having Hc-CDR1, Hc-CDR2 and Hc-CDR3 amino acid sequences shown in SEQ ID NOs: 12 and Lc-CDR1 Lc-CDR2, and Lc-CDR3 amino acid sequences as shown in SEQ ID NOs: 11.

Another aspect of the invention is an isolated antibody having Hc-CDR1, Hc-CDR2 and Hc-CDR3 amino acid sequences shown in SEQ ID NOs: 14 and Lc-CDR1 Lc-CDR2, and Lc-CDR3 amino acid sequences as shown in SEQ ID NOs: 13.

Another aspect of the invention is an isolated antibody having Hc-CDR1, Hc-CDR2 and Hc-CDR3 amino acid sequences shown in SEQ ID NOs: 16 and Lc-CDR1 Lc-CDR2, and Lc-CDR3 amino acid sequences as shown in SEQ ID NOs: 15.

Another aspect of the invention is an isolated polynucleotide encoding an antibody of the invention.

In another aspect, the invention relates to an antibody which binds to a common epitope defined by antibody 4A5 and 5F6, and/or which compete for binding to the CD147 with antibody 4A5 or 5F6 or which have other functional binding characteristics exhibited by antibody 4A5 and 5F6 such as protecting against D2-exchange at residues 65-74 of SEQ ID NO: 1. Such antibodies include, for example, those which compete with antibody 4A5 or 5F6 and bind to CD147 with a dissociation constant (K$_D$) of 10$^{-7}$ M or less, such as of 10$^{-8}$ M or less, 10$^{-9}$ M or less, 10$^{-10}$ M or less, or even lower (e.g., 10$^{-11}$ M or less).

The present invention provides specific binding domains derived from exemplary antibody sequences capable of binding to human CD147 as defined herein and which block activities associated with one or more bioactivities associated with CD147 including but not limited to angiogenesis, VEGF production, and matrix metalloproteinase production (MMP-1, MMP-2, and/or MMP-9 production). Specific binding domains are those domains specified as the variable regions and CDR residues as specified within SEQ ID NOS: 9-16. The invention further includes antibodies derived from SEQ ID NOS: 9-16 such as humanized or reshaped antibodies or antibody binding domains that retain the ability to immunospecifically bind to human CD147 with an affinity of KD of 10$^{-7}$ M or less, compete with antibody 2H3, 4A5, or 5F6 for binding to CD147, and block the bioactivities of CD147.

Thus, one aspect of the invention relates to a humanized antibody comprising a humanized heavy chain and humanized light chain, wherein:

(1) the humanized heavy chain variable region comprise three complementarity determining regions (CDRS) from the mouse 2H3, 4A5, 5F6 or 2C8 heavy chain and a framework from a human acceptor antibody heavy chain, optionally having one or more human framework residue substitutions, and (2) the humanized light chain variable region comprises three complementarity determining regions from the mouse 2H3, 4A5, 5F6 or 2C8 light chain and a framework from a human acceptor antibody light chain optionally having one or more human framework residue substitutions; and the humanized antibody specifically binds to human CD147.

In a further embodiment, the humanized antibody may be composed of one or more CDRs that are further engineered with one or more substitutions or deletions, for example, those that are 90%, 95%, 98% or 99.5% identical to one or more CDRs of 2H3, 4A5, 5F6 or 2C8.

Another embodiment relates to the treatment or prevention of pathological conditions associated with CD147 bioactivity by administering a therapeutically or prophylactically effective amount of one antibody of the present invention or a mixture of antibodies of the present invention to a subject in need of such treatment.

In a further embodiment, there are provided antigen epitopes as a component of a vaccine. The epitopes described above comprising SEQ ID NO: 1 residues 65-74 or conservative changes thereof which are still recognized by the antibodies of the invention, are useful for actively immunizing a host to elicit production of antibodies against CD147 capable of the combating or preventing pathological conditions associated with CD147 bioactivity.

BRIEF DESCRIPTION OF THE DRAWINGS

FIG. 1 shows a domain map of human CD147 isoform 2 and the sequence of the propeptide in single letter amino acid code.

FIG. 4 shows the effect of the Akt-v, an Akt-dependent signaling pathway inhibitor, on CD147 ECD or subdomain Fc-constructs used stimulate secretions of (A) VEGF or (B) MMP-1.

FIG. 5 shows bar graphs of murine antibody (10 ug/ml) binding (mIgG1) to live MDA-MB-231 cells (A) but not NHLF cells (B).

FIG. 12 shows a simplified H/D exchange maps of the Asp19-Asn117 construct complexed with either 4A5 (top) or 5F6 (bottom) binding regions.

BRIEF DESCRIPTION OF THE SEQUENCE LISTING

Figure 2:
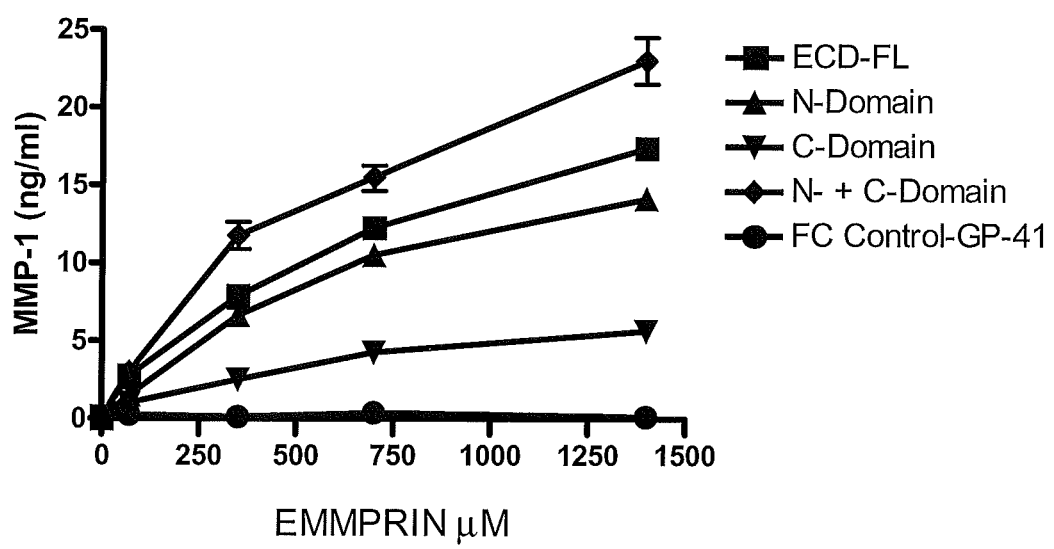
FIG. 2 is a graph showing the relative activity of CD147 ECD and subdomains (N-Domain is residues 19-117, C-Domain residues 95-204) as Fc-constructs in concentration-dependent stimulation MMP-1 production in NHLF.

| SEQ ID NO: | DESCRIPTION | Features, Abbreviations |
|---|---|---|
| 1 | Human CD147, propolypeptide | 269 aa |
| 2 | Human CD147 N-domain Forward Primer | 5' TCGAGGTACCGCCACCATG GCGGC 3' |
| 3 | Human CD147 N-domain Reverse Primer | 5' TGCAGCGGCCGCCGTTGAT GTGTTCTGACG 3' |
| 4 | Human CD147 C-domain Forward Primer | 5' CAAGAGGGATCCGCCGGCA CGGCC 3' |
| 5 | Human CD147 C-domain Reverse Primer | 5' TGCAGCGGCCGCTGCGCAC GCGG 3' |
| 6 | Rat HC-1 | 5' - TGGGCTACGYTGCAGGTGA C |
| 7 | Rat LC-1 | 5' - CTCATGCTGTACGTGCTGTC |
| 8 | Rat LC-2 | 5' - CTTGACATTGATGTCTTTGG |
| 9 | 2H3 LC Variable | CDR1 residues 27 to 38 CDR2 residues 56 to 58 CDR3 residues 95 to 103 |
| 10 | 2H3 HC Variable | CDR1 residues 25 to 32 CDR2 residues 50 to 57 CDR3 residues 96 to 109 |
| 11 | 4A5 LC Variable | CDR1 residues 27 to 38 CDR2 residues 56 to 58 CDR3 residues 95 to 102 |
| 12 | 4A5 HC Variable | CDR1 residues 26 to 33 CDR2 residues 51 to 58 CDR3 residues 97 to 109 |
| 13 | 5F6 LC Variable | CDR1 residues 27 to 32 CDR2 residues 50 to 52 CDR3 residues 89 to 97 |
| 14 | 5F6 HC Variable | CDR1 residues 26 to 33 CDR2 residues 51 to 60 CDR3 residues 99 to 105 |
| 15 | 2C8 LC Variable | CDR1 residues 27 to 32 CDR2 residues 50 to 52 CDR3 residues 89 to 97 |
| 16 | 2C8 HC Variable | CDR1 residues 26 to 33 CDR2 residues 51 to 60 CDR3 residues 99 to 105 |

DETAILED DESCRIPTION

Abbreviations

CDR—complementarity determining region; HC—heavy chain; GvHD graft-versus-host disease; LC—light chain; IFN—interferon (a, alpha; b, beta); Ig—immunoglobulin; mAB—monoclonal antibody; MMP—matrix metalloproteinase; NHLF—normal human lung fibroblasts; NHDF—normal human dermal fibroblasts; VEGF—vascular endothelial growth factor; VL—Variable light chain; VH—Variable heavy chain Definitions As used herein, an "antibody" includes whole antibodies and any antigen binding fragment or a single chain thereof. Thus, the antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, which can be incorporated into an antibody of the present invention. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments to a preselected target. Examples of binding fragments encompassed within the term "antigen binding portion" of an antibody include (i) a Fab fragment, a monovalent fragment consisting of the VL, VH, CL and CH, domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (I 988) Science 242:423-426, and Huston et al. (1988) Proc. Natl. Acad Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Conversely, libraries of scFv constructs can be used to screen for antigen binding capability and then, using conventional techniques, spliced to other DNA encoding human germline gene sequences. One example of such a library is the "HuCAL: Human Combinatorial Antibody Library" (Knappik, A. et al. J Mol Biol (2000) 296(1):57-86).

The term "CDR" refers to the complementarity determining region or hypervariable region amino acid residues of an antibody which are responsible for antigen-binding. The hypervariable region or "CDR"s of the human IgG subtype of antibody comprise amino acid residues from residues 24-34

(L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)] and/or those residues from a hypervariable loop (i.e., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., J. Mol. Biol. 196: 901-917 (1987)]. Framework or FR1-4 residues are those variable domain residues other than and bracketing the hypervariable regions. More recently, a universal numbering system has been developed and widely adopted, international ImMunoGeneTics information System® (IMGT) (LaFranc, et al. 2005. Nucl Acids Res. 33:D593-D597). Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information is used in grafting and replacement of CDR residues from immunoglobulins of one species into an acceptor framework from, typically, a human antibody.

The term "EMMPRIN" is used herein to mean "Extracellular Matrix Metalloprotein Inducer", CD147, the product of the human basigin (BSG) gene, human leukocyte activation antigen M6, the species homologue of rat OX-47, mouse basigin, and chicken HT7 molecule, tumor cell-derived collagenase stimulatory factor, neurothelin and include all of the variants, isoforms and species homologs of CD147. Accordingly, the antibodies of the invention may, in certain cases, cross-react with CD147 from species other than human. In other cases, the antibodies may be completely specific for human CD147 and not exhibit species or other types of cross-reactivity.

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents.

"Humanization" (also called Reshaping or CDR-grafting) includes established techniques for reducing the immunogenicity of monoclonal antibodies (mAbs) from xenogeneic sources (commonly rodent) and for improving affinity or the effector functions (ADCC, complement activation, C1q binding). The engineered mAb can be produced using the techniques of molecular biology, using phage displayed randomized sequences, or synthesized de novo. For example, in order to construct a humanized antibody with incorporated CDR regions from a nonhuman species, the design might include variations such as conservative amino acid substitutions in residues of the CDRs, and back substitution of residues from the nonhuman mAb into the human framework regions (backmutations). The positions can be discerned or identified by sequence comparison methods, consensus sequence analysis, or structural analysis of the variable regions' 3D structure. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way or by simple sequence alignment algorithms (e.g. Clustal W), FR (framework) residues can be selected from known antibody sequences, found in such publicly accessible databases as VBASE or Kabat, and the consensus sequences optimized so that the desired antibody characteristic, such as affinity for the target antigen(s), is achieved. As the datasets of known parameters for antibody structures increases, so does the sophistication and refinement of these techniques. Another approach to humanization is to modify only surface residues of the rodent sequence with the most common residues found in human mAbs and has been termed "resurfacing" or "veneering". A large number of both human and non-human Ig sequences are now known and freely available and used by those skilled in the art, e.g. the database and tools developed by of LeFranc et al found under the name IMGT; websites created by the U.S. National Center for Biologics (NCBI); Kabat et al., Sequences of Proteins of Immunological Interest, U.S. Dept. Health (1983) now also greatly expanded and available online, each entirely incorporated herein by reference. Humanization or engineering of antibodies of the present invention can be performed using any method known or those developed using human immunoglobulin sequence information. Such methods are taught in, for example, Winter U.S. Pat. No. 6,982,361 and Bowdish et al. WO03/025019, the contents of which are incorporated herein by reference.

As used herein, $K_D$ refers to the dissociation constant, specifically, the antibody $K_D$ for a predetermined antigen, and is a measure of affinity of the antibody for a specific target. High affinity antibodies have a $K_D$ of $10^{-8}$ M or less, more preferably $10^{-9}$ M or less and even more preferably $10^{-10}$ M or less, for a predetermined antigen. The reciprocal of $K_D$ is $K_A$, the association constant. The term "$k_{dis}$" or "$k_2$", or "$k_d$" as used herein, is intended to refer to the dissociation rate of a particular antibody-antigen interaction. The "$K_D$", is the ratio of the rate of dissociation ($k_2$), also called the "off-rate ($k_{off}$)", to the rate of association rate ($k_1$) or "on-rate ($k_{on}$)". Thus, $K_D$ equals $k_2/k_1$ or $k_{off}/k_{on}$ and is expressed as a molar concentration (M). It follows that the smaller the $K_D$, the stronger the binding. Thus, a $K_D$ of $10^{-6}$ M (or 1 microM) indicates weak binding compared to $10^{-9}$ M (or 1 nM).

The terms "monoclonal antibody" or "monoclonal antibody composition" as used herein refer to a preparation of antibody molecules of single molecular composition. A monoclonal antibody composition displays a single binding specificity and affinity for a particular epitope. The term also includes "recombinant antibody" and "recombinant monoclonal antibody" as all antibodies are prepared, expressed, created or isolated by recombinant means, such as (a) antibodies isolated from an animal or a hybridoma prepared by the fusion of antibody secreting animal cells and an fusion partner, (b) antibodies isolated from a host cell transformed to express the antibody, e.g., from a transfectoma, (c) antibodies isolated from a recombinant, combinatorial human or other species antibody library, and (d) antibodies prepared, expressed, created or isolated by any other means that involve splicing of immunoglobulin gene sequences to other DNA sequences. An "isolated antibody," as used herein, is intended to refer to an antibody which is substantially free of other antibodies having different antigenic specificities. An isolated antibody that specifically binds to an epitope, isoform or variant of human CD147 may, however, have cross-reactivity to other related antigens, e.g., from other species (e.g., CD147 species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding", "immunospecific binding" and "binds immunospecifically" refers to antibody binding to a predetermined antigen. Typically, the antibody binds with a dissociation constant ($K_D$) of $10^{-7}$ M or less, and binds to the predetermined antigen with a $K_D$ that is at least twofold less than its $K_D$ for binding to a non-specific antigen (e.g., BSA, casein, or any other specified polypeptide) other than the predetermined antigen. The phrases "an antibody recognizing an antigen" and "an antibody specific for an antigen" are used interchangeably herein with the term "an antibody which binds specifically to an antigen". As used herein "highly specific" binding means that the relative $K_D$ of the antibody for the specific target epitope is at least 10-fold less than the $K_D$ for binding that antibody to other ligands.

As used herein, "isotype" refers to the antibody class (e.g., IgM or IgG) that is encoded by heavy chain constant region genes. Some antibody classes further encompass subclasses which are also encoded by the heavy chain constant regions and further decorated by oligosaccharides at specific residues within the constant region domains (e.g. IgG1, IgG2, IgG3 and IgG4) which further impart biological functions to the antibody. For example, in human antibody isotypes IgG1, IgG3 and to a lesser extant, IgG2 display effector functions as do murine IgG2a antibodies.

By "effector" functions or "effector positive" is meant that the antibody comprises domains distinct from the antigen specific binding domains capable of interacting with receptors or other blood components such as complement, leading to, for example, the recruitment of macrophages and events leading to destruction of cells bound by the antigen binding domains of the antibody. Antibodies have several effector functions mediated by binding of effector molecules. For example, binding of the C1 component of complement to antibodies activates the complement system. Activation of complement is important in the opsonisation and lysis of cell pathogens. The activation of complement stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Antibodies of the Invention

A CD147 antibody of the invention is an antibody that inhibits, blocks, or interferes with at least one CD147 activity or binding, or with CD147 activity or binding, in vitro, in situ and/or in vivo. A suitable anti-CD147 antibody, specified portion, or variant can also optionally affect at least one CD147 activity or function, such as but not limited to, RNA, DNA or protein synthesis, protein release, CD147 receptor signaling, CD147 cleavage, CD147 activity, CD147 production and/or synthesis.

In one embodiment, the anti-human CD147 antibody, has a binding region comprising a light chain variable (VL) or heavy chain variable (VH) region having the amino acid sequence as shown in SEQ ID NO: 9-16 and which antibody or binding portion thereof immunospecifically binds CD147. In another embodiment of the invention, the antibody or antigen binding portion thereof, binds to CD147 protein and, in addition, the antibodies possesses specified functional properties of antibodies of the invention, such as:

binding to human CD147 in ELISA;
inhibition of human CD147 binding to MDA-MB-231 breast carcinoma cells;
inhibition of human CD147 mediated MMP-1 release from NHLF with an IC50 which is less than or equal to that of Fab 5F6;
inhibition of tumor cell-mediated release of MMP-2 from human fibroblast cells;
inhibition of human CD147 mediated VEGF release stimulation;
binding to human CD147 with Kd of less than 100 nM ($10^{-7}$ M);
binding to cynomolgus monkey CD147 with a $K_D$ of less than 100 nM, and more preferably, less than 10 nM; and
binds to an epitope on human CD147 isoform 2 encompassed by the residues 65-74 of SEQ ID NO: 1 (DALPGQKTEF).

In another aspect of the invention, the structural features of the 2H3, 5F6, or 4A5 binding domain, are used to create structurally related human anti-CD147 antibodies that retain at least one functional property of the antibodies of the invention, such as binding to CD147. More specifically, one or more CDR regions of 2H3, 5F6, or 4A5 (specified residues of SEQ ID NO: 9-14) can be combined recombinantly with known human framework regions and CDRs to create additional, recombinantly-engineered, human anti-CD147 antibodies of the invention.

Since it is well known in the art that antibody heavy and light chains CDR domains play a particularly important role in the binding specificity/affinity of an antibody for an antigen, the recombinant antibodies of the invention prepared as set forth above preferably comprise the light and heavy chain CDR3s of 2H3 (SEQ ID NO: 9 and 10, respectively). The antibodies further can comprise the CDR2s of 2H3. The antibodies further can comprise the CDR1s of 2H3. Accordingly, the invention further provides anti-CD147 antibodies comprising: (1) human heavy chain framework regions, a human heavy chain CDR1 region, a human heavy chain CDR2 region, and a human heavy chain CDR3 region, wherein the human heavy chain CDR3 region is selected from the CDR3s of 2H3 as shown in SEQ ID NO: 10, and (2) human light chain framework regions, a human light chain CDR1 region, a human light chain CDR2 region, and a human light chain CDR3 region, wherein the human light chain CDR3 region is selected from the CDR3s of 2H3 as shown in SEQ ID NO: 9, wherein the antibody binds CD147. The antibody may further comprise the heavy chain CDR2 and/or the light chain CDR2 of 2H3. The antibody may further comprise the heavy chain CDR1 and/or the light chain CDR1 of 2H3.

As a non-limiting example, the antibody or antigen-binding portion or variant can comprise at least one of the heavy chain CDR3 having the amino acid sequence as described herein and selected from the group consisting of SEQ ID NO: 10, 12, 14, or 16 and/or a light chain CDR3 having the amino acid sequence of SEQ ID NO: 9, 11, 13, and 15. In a particular embodiment, the antibody or antigen-binding fragment can have an antigen-binding region that comprises at least a portion of at least one heavy chain CDR (i.e., CDR1, CDR2 and/or CDR3) having the amino acid sequence as described herein and selected from the group consisting of SEQ ID NO: 10, 12, 14, or 16. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 amino acid sequence as described herein and selected from the group consisting of SEQ ID NO: 9, 11, 13, and 15. In a preferred embodiment the three heavy chain CDRs and the three light chain CDRs of the antibody or antigen-binding fragment have the amino acid sequence of the corresponding CDR of at least one of mAb 2H3, 5F6, 4A5, and 2C8, as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

In one embodiment, the engineered antibodies of the invention have the exact sequence, CDR1, 2, and/or 3; of 2H3, 5F6, 4A5, and 2C8. In addition to engineered antibodies wherein the CDR is grafted into e.g. a human framework, the ordinarily skilled artisan will appreciate that some deviation from the exact CDR sequences of original murine antibodies may be possible or desirable while still retaining the ability of the antibody to bind CD147 effectively (e.g., conservative substitutions). Accordingly, in another embodiment, the engineered antibody may be composed of one or more CDRs that are, for example, 90%, 95%, 98% or 99.5% identical to one or more CDRs of those variable regions as specified in SEQ ID NO: 9-16. In addition to simply binding CD147, engineered antibodies such as those described above may be selected for their retention of other functional properties of antibodies of the invention, such as the ability to inhibit angiogenesis resulting in growth inhibition of tumor cells in vivo. Human monoclonal antibodies of the invention can be tested for binding to CD147 by, for example, standard ELISA.

In another embodiment, the epitope bound by the antibodies of the invention, more specifically 65-74 of SEQ ID NO: 1 (DALPGQKTEF) or a nucleic acid coding sequence therefore, can be used to immunize a subject in order to produce the antibodies of the invention directly in the host for the purpose of treating, preventing, or ameliorating disease or symptoms of disease associated with the production of CD147.

Generation of Anti-CD147 Antibodies

Anti-CD147 antibodies of the present invention can be optionally produced by a variety of techniques, including the standard somatic cell hybridization technique (hybridoma method) of Kohler and Milstein (1975) Nature 256:495. In the hybridoma method, a mouse or other appropriate host animal, such as a hamster or macaque monkey, is immunized as described herein to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The anti-CD147 antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-CD147 antibody can be isolated from such animals and immortalized using suitable methods, such as the methods described herein. Alternatively, the antibody coding sequences may be cloned, introduced into a suitable vector, and used to transfect a host cell for expression and isolation of the antibody by methods taught herein and those known in the art.

The use of transgenic mice carrying human immunoglobulin (Ig) loci in their germline configuration provide for the isolation of high affinity fully human monoclonal antibodies directed against a variety of targets including human self antigens for which the normal human immune system is tolerant (Lonberg, N. et al., U.S. Pat. No. 5,569,825, U.S. Pat. No. 6,300,129 and 1994, Nature 368:856-9; Green, L. et al., 1994, Nature Genet. 7:13-21; Green, L. & Jakobovits, 1998, Exp. Med. 188:483-95; Lonberg, N. and Huszar, D., 1995, Int. Rev. Immunol. 13:65-93; Kucherlapati, et al. U.S. Pat. No. 6,713,610; Bruggemann, M. et al., 1991, Eur. J. Immunol. 21:1323-1326; Fishwild, D. et al., 1996, Nat. Biotechnol. 14:845-851; Mendez, M. et al., 1997, Nat. Genet. 15:146-156; Green, L., 1999, J. Immunol. Methods 231:11-23; Yang, X. et al., 1999, Cancer Res. 59:1236-1243; Brüggemann, M. and Taussig, M J., Curr. Opin. Biotechnol. 8:455-458, 1997; Tomizuka et al. WO02043478). The endogenous immunoglobulin loci in such mice can be disrupted or deleted to eliminate the capacity of the animal to produce antibodies encoded by endogenous genes. In addition, companies such as Abgenix, Inc. (Freemont, Calif.) and Medarex (San Jose, Calif.) can be engaged to provide human antibodies directed against a selected antigen using technology as described above.

In another embodiment, the human antibody is selected from a phage library, where that phage comprises human immunoglobulin genes and the library expresses human antibody binding domains as, for example, single chain antibodies (scFv), as Fab, or some other construct exhibiting paired or unpaired antibody variable regions (Vaughan et lo al. Nature Biotechnology 14:309-314 (1996): Sheets et al. PITAS (USA) 95:6157-6162 (1998)); Hoogenboom and Winter, J. Mol. Biol., 227:381 (1991); Marks et al. J. Mol. Biol., 222:581 (1991)). Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5, 580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582, 915 and 6,593,081 to Griffiths et al.

Preparation of immunogenic antigens, and monoclonal antibody production can be performed using any suitable technique such as recombinant protein production. The immunogenic antigens can be administered to an animal in the form of purified protein, or protein mixtures including whole cells or cell or tissue extracts, or the antigen can be formed de novo in the animal's body from nucleic acids encoding said antigen or a portion thereof.

The isolated nucleic acids of the present invention can be made using (a) recombinant methods, (b) synthetic techniques, (c) purification techniques, or combinations thereof, as well-known in the art. DNA encoding the monoclonal antibodies is readily isolated and sequenced using methods known in the art (e.g., by using oligonucleotide probes that are capable of binding specifically to genes encoding the heavy and light chains of murine antibodies). Where a hybridoma is produced, such cells can serve as a source of such DNA. Alternatively, using display techniques wherein the coding sequence and the translation product are linked, such as phage or ribosomal display libraries, the selection of the binder and the nucleic acid is simplified. After phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria.

Humanized Antibodies

The invention further provides humanized immunoglobulins (or antibodies) which bind human CD147. The humanized forms of immunoglobulins have variable framework region(s) substantially from a human immunoglobulin (termed an acceptor immunoglobulin) and CDRs substantially from a non-human mAbs which specifically binds CD147. The constant region(s), if present, are also substantially from a human immunoglobulin. The humanized antibodies exhibit $K_D$ for CD147 of at least about 10^-6 M (1 microM), about 10^-7 M (100 nM), or less. The binding affinity of the humanized antibodies may be greater or less than that of the mouse antibody from which they were derived. To affect a change in affinity, improve affinity, of the humanized antibody for CD147 substitutions in either the CDR residues or the human residues may be made.

The source for production of humanized antibody which binds to CD147 is preferably the 2H3, 4A5, 5F6 or 2C8 mouse antibodies whose generation, isolation and characterization are described in the Examples provided herein, although other mouse antibodies, which compete with the 2H3, 4A5, 5F6 or 2C8 mouse antibodies for binding to CD147 can also be used. The identified CDRs of SEQ ID NO: 9-16 are, thus, the starting point of the humanization process.

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies, be derived from human germline immunoglobulin sequences, or can be consensus sequences of several human antibody and/or germline sequences.

Suitable human antibody sequences are identified by computer comparisons of the amino acid sequences of the mouse variable regions with the sequences of known human antibodies. The comparison is performed separately for heavy and light chains but the principles are similar for each.

In one example, the amino acid sequence of anti-CD147 mAb is used to query a human antibody database compiled from public antibody sequence databases. The heavy chain variable region of SEQ ID NO: 10, 12, 14, or 16 can be used to find the human variable region with the highest sequence identity. The variable region of the light chain of SEQ ID NO: 9, 11, 13, or 15 can, similarly, be used to find the human variable region with the highest sequence identity. A DNA construct in which the regions coding for the CDRs of one of the heavy chain variable regions from the murine mAbs donor are transferred into the selected human heavy chain variable sequence, replacing the CDRs of the human variable region is prepared for each murine variable region.

The unnatural juxtaposition of murine CDR regions with human variable framework region can result in unnatural conformational restraints, which, unless corrected by substitution of certain amino acid residues, lead to loss of binding affinity. As noted supra, the humanized antibodies of the invention comprise variable framework region(s) substantially from a human immunoglobulin and CDRs substantially from a mouse immunoglobulin (e.g., 2H3, 4A5, 5F6 or 2C8 mouse antibodies). Having identified the CDRs of mouse antibodies and appropriate human acceptor immunoglobulin sequences, the next step is to determine which, if any, residues from these components should be substituted to optimize the properties of the resulting humanized antibody. In general, substitution of human amino acid residues with murine should be minimized, because introduction of murine residues increases the risk of the antibody eliciting a HAMA response in humans. Amino acids are selected for substitution based on their possible influence on CDR conformation and/or binding to antigen. Investigation of such possible influences can be done by modeling, examination of the characteristics of the amino acids at particular locations, or empirical observation of the effects of substitution or mutagenesis of particular amino acids. With regard to the empirical method, it has been found to be particularly convenient to create a library of variant sequences that can be screened for the desired activity, binding affinity or specificity. One format for creation of such a library of variants is a phage display vector. Alternatively, variants can be generated using other methods for varigation of a nucleic acid sequence encoding the targeted residues within the variable domain.

Another method of determining whether further substitutions are required, and the selection of amino acid residues for substitution, can be accomplished using computer modeling. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity is/are selected as starting points for construction of the molecular model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

Usually the CDR regions in humanized antibodies are substantially identical, and more usually, identical to the corresponding CDR regions in the mouse antibody from which they were derived. Although not usually desirable, it is sometimes possible to make one or more conservative amino acid substitutions of CDR residues without appreciably affecting the binding affinity of the resulting humanized immunoglobulin. Occasionally, substitutions of CDR regions can enhance binding affinity.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin.

Because of the degeneracy of the code, a variety of nucleic acid sequences will encode each immunoglobulin amino acid sequence. The desired nucleic acid sequences can be produced by de nova solid-phase DNA synthesis or by PCR mutagenesis of an earlier prepared variant of the desired polynucleotide. All nucleic acids encoding the antibodies described in this application are expressly included in the invention.

The variable segments of humanized antibodies produced as described supra are typically linked to at least a portion of a human immunoglobulin constant region. The antibody will contain both light chain and heavy chain constant regions. The heavy chain constant region usually includes CH1, hinge, CH2, CH3, and, sometimes, CH4 domains.

The humanized antibodies may comprise any type of constant domains from any class of antibody, including IgM, IgG, IgD, IgA and IgE, and any subclass (isotype), including IgG1, IgG2, IgG3 and IgG4. When it is desired that the humanized antibody exhibit cytotoxic activity, the constant domain is usually a complement-fixing constant domain and the class is typically $IgG_1$. When such cytotoxic activity is not desirable, the constant domain may be of the $IgG_2$ class. The humanized antibody may comprise sequences from more than one class or isotype.

Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence (see Queen et al., Proc. Natl. Acad. Sci. USA 86, 10029 (1989); WO 90/07861; Co et al., J. Immunol. 148, 1149 (1992), which are incorporated herein by reference in their entirety for all purposes).

Methods of Using the Antibodies

As described in detail below, the present inventors three of the isolated monoclonal antibodies (2H3, 4A5, 5F6) bind overlapping epitopes on CD147 and display in vitro and/or in vivo CD147 inhibiting activities. Significantly, the reactivity of the mAbs includes the ability to reduce MMP and VEGF production, and inhibit angiogenesis.

Given the properties of the monoclonal antibodies as described in the present invention, the antibodies or antigen binding fragments thereof are suitable both as therapeutic and prophylactic agents for treating or preventing CD147-associated conditions in humans and animals.

In general, use will comprise administering a therapeutically or prophylactically effective amount of one or more monoclonal antibodies or antigen binding fragments of the present invention to a susceptible subject or one exhibiting a condition in which CD147 activity is known to have pathological sequelae such as tumor growth and metastasis. Any active form of the antibody can be administered, including Fab and F(ab')2 fragments.

Preferably, the antibodies used are compatible with the recipient species such that the immune response to the mAb does not result in an unacceptably short circulating half-life or induce an immune response to the mAb in the subject. Preferably, the mAb administered exhibit some secondary functions such as binding to Fc receptors of the subject and activation of ADCC mechanisms.

Treatment of individuals may comprise the administration of a therapeutically effective amount of the antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to CD147, or an antibody capable of protecting against CD147 in a recipient patient, the dosage of administered agent will vary depending upon such factors as the patient's age, weight, height, sex, general medical condition, previous medical history, etc.

In general, if administering a systemic dose of the antibody, it is desirable to provide the recipient with a dosage of antibody which is in the range of from about 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg (body weight of recipient), although a lower or higher dosage may be administered. Dosages as low as about 1.0 mg/kg may be expected to show some efficacy. Preferably, about 5 mg/kg is an acceptable dosage, although dosage levels up to about 50 mg/kg are also preferred especially for therapeutic use. Alternatively, administration of a specific amount of the antibody may be given which is not based upon the weight of the patient such as an amount in the range of 1 ug-100 ug, 1 mg-100 mg, or 1 gm-100 gm. For example, site specific administration may be to body compartment or cavity such as intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, vaginal, rectal, buccal, sublingual, intranasal, or transdermal means.

The CD147 antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

In a similar approach, another therapeutic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-CD147 response (Linthicum, D. S, and Farid, N. R., Anti-Idiotypes, Receptors, and Molecular Mimicry (1988), pp 1-5 and 285-300).

Likewise, active immunization can be induced by administering one or more antigenic and/or immunogenic epitopes as a component of a vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used e.g., NH2-acetylation or COOH-terminal amidation, to provide additional means for coupling or fusing the peptide to another protein or peptide molecule or to a support.

The antibodies capable of protecting against CD147 bioactivity are intended to be provided to recipient subjects in an amount sufficient to effect a reduction, resolution, or amelioration in the CD147-related symptom or pathology. An amount is said to be sufficient or a "therapeutically effective amount" to "effect" the reduction of symptoms if the dosage, route of administration, etc. of the agent are sufficient to influence such a response. Responses to antibody administration can be measured by analysis of subject's affected tissues, organs, or cells as by imaging techniques or by ex vivo analysis of tissue samples. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle. Additional pharmaceutical methods may be employed to control the duration of action. Controlled release preparations may be achieved through the use of polymers to complex or absorb the compounds. Another possible method to control the duration of action by controlled release preparations is to incorporate the compounds of the present invention into particles of a polymeric material such as polyesters, polyamino acids, hydrogels, poly(lacticacid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container containing or packaged in association with the above-described antibodies. The kit may also comprise another container containing or packaged in association solutions necessary or convenient for carrying out the invention. The containers can be made of glass, plastic or foil and can be a vial, bottle, pouch, tube, bag, etc. The kit may also contain written information, such as procedures for carrying out the present invention or analytical information, such as the amount of reagent contained in the first container means. The container may be in another container apparatus, e.g. a box or a bag, along with the written information.

Yet another aspect of the present invention is a kit for detecting CD147 in a biological sample. The kit includes a container holding one or more antibodies which binds an epitope of CD147 and instructions for using the antibody for the purpose of binding to CD147 to form an immunological complex and detecting the formation of the immunological complex such that the presence or absence of the immunological complex correlates with presence or absence of CD147 in the sample. Examples of containers include multi-well plates which allow simultaneous detection of CD147 in multiple samples.

Therapeutic Applications

The anti-CD147 antibodies of the present invention, antigen binding fragments, or specified variants thereof can be used to measure or cause effects in an cell, tissue, organ or animal (including mammals and humans), to diagnose, monitor, modulate, treat, alleviate, help prevent the incidence of, or reduce the symptoms of, a condition mediated, affected or modulated by CD147. Such conditions are selected from, but not limited to, diseases or conditions mediated by cell migration and tissue remodeling as e.g. in tissue regrowth, neoplastic disease, metastatic disease, and fibrotic conditions. Such diseases or conditions include especially malignant and neurologic disorder or disease, or other known or specified CD147 related conditions which may accompany an inflammatory or autoimmune disorder or disease, a cardiovascular disorder or disease, or an infection. In particular, the antibodies are useful for the treatment of diseases that involve angiogenesis such as disease of the eye and neoplastic disease, tissue remodeling such as restenosis, and proliferation of certain cells types particularly epithelial and squamous cell carcinomas. Particular indications include use in the treatment of atherosclerosis, restenosis, cancer metastasis, rheumatoid arthritis, diabetic retinopathy and macular degeneration. The neutralizing antibodies of the invention are also useful to prevent or treat unwanted bone resorption or degradation, for example as found in osteoporosis or resulting from PTHrP overexpression by some tumors. The antibodies may also be useful in the treatment of various fibrotic diseases such as idiopathic pulmonary fibrosis, diabetic nephropathy, hepatitis, and cirrhosis.

Thus, the present invention provides a method for modulating or treating at least one CD147 related disease, in a cell, tissue, organ, animal, or patient, as known in the art or as described herein, using at least one CD147 antibody of the present invention. Particular indications are discussed below:

Pulmonary Disease

The present invention also provides a method for modulating or treating a pulmonary or pleural disease in a cell, tissue, organ, animal or patient, including, but not limited to, at least one of: pneumonia; lung abscess; occupational lung diseases caused be agents in the form or dusts, gases, or mists; asthma, bronchiolitis fibrosa obliterans, respiratory failure, hypersensitivity diseases of the lungs including hypersensitivity pneumonitis (extrinsic allergic alveolitis), allergic bronchopulmonary aspergillosis, and drug reactions; adult respiratory distress syndrome (ARDS), Goodpasture's Syndrome, chronic obstructive airway disorders (COPD), idiopathic interstitial lung diseases such as idiopathic pulmonary fibrosis and sarcoidosis, desquamative interstitial pneumonia, acute interstitial pneumonia, respiratory bronchiolitis-associated interstitial lung disease, idiopathic bronchiolitis obliterans with organizing pneumonia, lymphocytic interstitial pneumonitis, Langerhans' cell granulomatosis, idiopathic pulmonary hemosiderosis; acute bronchitis, pulmonary alveolar proteinosis, bronchiectasis, pleural disorders, atelectasis, cystic fibrosis, and tumors of the lung, and pulmonary embolism.

Malignant Disease

The present invention also provides a method for modulating or treating a malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, solid tumors as primary disease or as metastatic disease, Kaposi's sarcoma, colorectal carcinoma, pancreatic carcinoma, renal cell carcinoma, lung cancer including mesothelioma, breast cancer, nasopharyngeal carcinoma, malignant histiocytosis, paraneoplastic syndrome/hypercalcemia of malignancy, adenocarcinomas, squamous cell carcinomas, sarcomas, malignant melanoma, particularly metastatic melanoma, hemangioma, metastatic disease, cancer related bone resorption, cancer related bone pain, and the like.

Immune Related Disease

The present invention also provides a method for modulating or treating an immune related disease, in a cell, tissue, organ, animal, or patient including but not limited to rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, OKT3 therapy, anti-CD3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

Cardiovascular Disease

The present invention also provides a method for modulating or treating a cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like.

Neurologic Disease

The present invention also provides a method for modulating or treating at neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi. system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16$^{th}$ Edition, Merck & Company, Rahway, N.J. (1992).

Other Therapeutic Uses of Anti-CD147 Antibodies

In addition to the above described conditions and diseases, the present invention also provides a method for modulating or treating fibrotic conditions of various etiologies such as liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular pehpritis, lupus nephritis); dermal fibrosis (including but not limited to scleroderma, hypertrophic and keloid scarring, burns); myelofibrosis; Neurofibromatosis; fibroma; intestinal fibrosis; and fibrotic adhesions resulting from surgical procedures.

The present invention also provides a method for modulating or treating an infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, E. coli, hemolytic uremic syndrome, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitis/epidydimitis, *legionella*, lyme disease, influenza a, Epstein-Barr virus, vital-associated hemaphagocytic syndrome, vital encephalitis/aseptic meningitis, and the like.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

Example 1

CD147 Reagents and Methods

In order to generate and test anti-CD147 monocloncal antibodies, certain protein constructs were generated which represent all or portions the extracellular domains of CD147. CD147 polypeptides and mutated, truncated or deleted forms of CD147 or fusion proteins can be prepared for a variety of uses, including but not limited to the generation of antibodies, as reagents in diagnostic assays, as reagents in assays for screening for therapeutic compounds that can be used in the treatment or prevention of, e.g., HIV-1 infection, AIDS, RA and cancer, and as pharmaceutical reagents useful in the treatment of, e.g., HIV-1 infection, AIDS and AIDS-related disorders, RA and cancer.

The bsg gene product known as CD147 isoform II (NCBI Accession No. NP_940991, SEQ ID NO: 1) is a propolypeptide 269 amino acids in length comprised of a signal sequence, extracellular, transmembrane and intracellular domain.

FIG. 1 shows schematically the signal peptide, extracellular (ECD or ECD-FL) which includes an N-terminal Ig domain (N-terminal domain, a C2-type domain from residue 22 to 103) and a C-terminal Ig domain (C-terminal domain, a V-like domain from residue 105-199), transmembrane (TM) and intracellular (ICD) domains of CD147. Peptides corresponding to one or more these domains of CD147 in which one or more other the other regions or domains have been deleted, as well as fusion proteins in which the full-length ECD or one or the other Ig-like domains is fused to an unrelated protein (e.g., GST, FLAG, hex-HIS, and Fc-fusions) were constructed by recombinant methods known to those skilled in the art and expressed and purified from mammalian cell cultures. Such a human CD147-Fc chimera is comprising residues 24-205 of SEQ ID NO: 1 fused to a carboxy-terminal hexa-His tagged Fc region of a human IgG1 is also commercially available from R&D Systems, Inc.

The cDNA encoding human CD147 isoform 2 was obtained from ATCC IMAGE clone 3867352 or MGC-17700 (NCBI Accession No. BC009040, 1622 bp, complete cds) and three expression constructs were generated using this clone as a template.

i) Construct #3364: Human CD147 ECD$_{1-192}$

To generate expression vector 3364, the nucleotide sequence encoding amino acids 1-192, including the endogenous signal peptide and extracellular domain (ECD$_{1-192}$) of human CD147, was subcloned as C-terminally FLAG-tagged (3364) version into the expression vector p3XFLAG-CMV-14 (Sigma). The polypeptide monomer will contain human CD147 ECD as a C-terminal FLAG-tagged protein, amino acids Met 1 to Gly 192 fused to the FLAG peptide (Brizzard et al. Biotechniques. 1994 April; 16(4):730-5).

ii) Construct #3128: Human CD147 N-Domain

To generate expression vector 3128, the nucleotide sequence encoding amino acids 1-117, including the endogenous signal peptide and the first Ig-like domain (N-domain) of human CD147, was subcloned into pcDNA 3.1(+) using Ig1.FC.for, 5' TCGAGGTACCGCCACCATGGCGGC 3' (SEQ ID NO: 2) and Ig1.FC.rev, 5' TGCAGCGGCCGCCGTTGATGTGTTCTGACG 3' (SEQ ID NO: 3)

as a C-terminal Fc-fusion (3128). When matured in the ER and secreted, the N-terminus was found to be Asp 19 which represents a mutation in the leader codon which normally codes for A. In addition to Fc-fusion construct Asp 19-Asn117-IgG$_1$-Fc, the CD147 N-Domain Asp19-Asn119 was further used to construct tagged and Asp19-Asn117-hexahis species.

iii) Construct #3129: Human CD147 C-Domain

To generate expression vector 3129, the nucleotide sequence encoding the human growth hormone signal peptide and amino acids 95-203 which include the second Ig-like domain (C-domain) of human CD147, was subcloned into pcDNA 3.1(+) as a C-terminal Fc-fusion Ig2.FC. using 5' CAAGAGGGATCCGCCGGCACGGCC 3'; Ig2.FC. (SEQ ID NO: 4) as the forward and 5' TGCAGCGGCCGCTGCGCACGCGG 3' (SEQ ID NO: 5) as the reverse primers. When expressed in a mammalian host cell, matured in the ER, and secreted, the protein will form a homodimer representing amino acid residues gly 95 to ser204 fused human Fc-scaffold (hinge, CH2 and CH3 domain of an IgG1 (construct #3129). In addition to Fc-fusion construct, gly 95 to ser204 was further used to construct tagged and hexahis species These three constructs were expressed transiently in HEK 293 cells in serum-free conditions (SFMII) following transfection with the cationic lipid reagent Lipofectamine 2000 (Invitrogen). Cell supernatants were harvested 4 days post-transfection and purified on either an anti-FLAG (ECD-FLAG) or Protein-A resin (N & C domain Fc fusions). The purity was checked by SDS-PAGE and by N-terminal aa sequencing.

Hexa-His tagged reagents representing the ECD-FL (having Asp19-192 of SEQ ID NO: 1), N-terminal Ig-domain (Asp19 to Asp 117) and the C-terminal Ig-domain (Glu95 to Ser204) were constructed, expressed and purified in a similar manner.

Example 2

Biological Assays and Characterization of CD147-Derived Constructs

Direct Binding to CD147 ECD or Subdomains.

Enzyme-immunoassays (EIAs) were used to test hybridoma cell supernatants for the presence of anti-human CD147 mAbs. Briefly, plates (Nunc-Maxisorp) were coated overnight with human CD147 (ECD, N & C-domain proteins) at 1 mg/mL in PBS. After washing in 0.15 M saline containing 0.02% (w/v) Tween 20, the wells were blocked with 1% (w/v) bovine serum albumin (BSA) in PBS for 1 hr at 370 C. Undiluted hybridoma supernatants were incubated on coated plates for 1 hour at 37° C. The plates were washed and then incubated with HRP-labeled goat anti-murine IgG, Fc specific (Sigma) diluted 1:10,000 in 1% BSA/PBS for 30 minutes at 370 C. Plates were again washed then incubated for 15 minutes at RT with 100 mL/well of citrate-phosphate substrate solution (0.1 M citric acid and 0.2 M sodium phosphate, 0.01% hydrogen peroxide, and 1 mg/mL O-phenylenediamine dihydrochloride). Substrate development was stopped by the addition of 4N sulfuric acid at 25 mL/well and the absorbance was measured at 490 nm via an automated plate spectrophotometer.

Live Cell Binding Assay

The human breast carcinoma cell line MDA-MB-231 (ATCC HTB-26) was used as a CD147 positive cell throughout these studies. Briefly, 50,000 MDA-MB-231 cells were plated per well on 96 well plates. After overnight growth, cells were gently washed with 200 µl ice cold DMEM three times and blocked with 200 µl 10% FBS-DMEM with 30 minutes incubation at room temperature. 100 µl undiluted antibody supernatants were added after washing plates, then incubated at room temperature for one hour and plates were washed again. A secondary HRP-conjugated antibody was added at 1:5000 dilution, followed by incubation for one hour at room temperature, washing, and adding 50 µl/well developing buffer at room temperature for 15 minutes. Substrate development was stopped by the addition of 4N sulfuric acid at 25 µl/well and the absorbance was measured at 490 nm via an automated plate spectrophotometer.

MMP-1 Production in Fibroblast Cells

It has been well established that human fibroblasts secrete a variety of matrix-type metalloproteases (MMPs) in upon contact with human CD147 protein (Kataoka, H., et al., 1993 Cancer Res 53, 3154-3158; Sameshima, T., et al., 2000 Cancer Left 157, 177-184; Guo, H., et al., 1997 J Biol Chem 272, 24-27). Recombinant human CD147 constructs produced in Example 1: ECD, N-domain and C-domain of human CD147 were used to stimulate human fibroblasts. MMP-1 activity in serum-free medium conditioned by fibroblast cells treated with different amounts of recombinant CD147 proteins were quantitatively determined using an MMP-1 Activity Assay according to the product manual (R&D Systems, Minneapolis, Minn.). As performed, the assay measured the MMP-1 contained in 150 µl of standards or samples. MMP-1 was captured by anti-MMP-1 antibodies immobilized on the bottom of assay wells. The captured MMP-1 was subsequently activated with 4-aminophenylmercuric acetate (APMA). MMP substrate added into each well is cleaved by activated MMP-1 and the resulting fluorescence determined using a SpectraFluor Plus Plate Reader (TECAN, Research Triangle Park, N.C.) using excitation at 320 nm and emission at 405 nm.

The results (FIG. 2) indicate that the ECD-Fc construct maintains the highest level of activity in inducing MMP expression and a high proportion of the activity resides in the N-domain. The C-domain construct was relatively poor at inducing MMP expression from the cultured fibroblasts.

Tumor-Fibroblast Co-Culture MMP-2 and MMP-9 Release Assay

MDA-MB-231 cells were cultured in DMEM containing 10% FBS in a humidified cell culture incubator supplemented with 10% CO2. NHDF cells were cultured under conditions recommended by the supplier. Briefly, cells were cultured in Fibroblast Growth Medium containing 1 ug/ml hFGF, 5 µg/ml insulin, 50 µg/ml gentamicin, and 50 µg/ml amphotericin. At subconfluence, MDA-MB-231 cells and NHDF cells were separately trypsinized and suspended in new culturing medium (DMEM containing 10% FBS). 100,000 of NHDF cells were co-cultured with 100,000 of MDA-MB-231 breast cancer cells in 6 well plates for 24 hours. Cell co-culture was gently rinsed with PBS and the growth medium was replaced with fresh serum-free DMEM medium and added 100 µl test antibody supernatants. After 3 days, culturing medium was again replaced with 1.5 ml of serum-free DMEM medium and the same amount of antibody supernatants. Conditioned media was collected two days later for analysis of activity. SDS substrate zymography electrophoresis was performed based on a previously described method with modifications (Tang, Y., et al., Mol Cancer Res 2, 73-80, 2004; Tang, Y., et al., Cancer Res 65, 3193-3199, 2005). Samples of conditioned medium containing 20 mg of protein were mixed with non-reducing SDS sample buffer and separated on a 10% polyacrylamide gel containing 0.1% gelatin. After electrophoresis, gels were washed with 2.5% Triton X-100 for 30 minutes. Substrate digestion was carried out by incubating the gel in 50 mM Tris-HCl (pH7.6) containing 5 mM CaCl2, 1 mM ZnCl2, 1% Triton X-100, and 0.02% NaN3 at 370 C for 24 hours. The gel was stained with 0.1% Coomassie Brilliant Blue 8250, and the location of gelatinolytic activity was detected as clear bands in the background of uniform blue staining. MMP standards were used to identify the position of bands having gelatinase activity.

Promotion of VEGF Secretion

VEGF production is stimulated by recombinant CD147s in fibroblast cells. It was previously established that recombinant CD147 can stimulate VEGF production in fibroblast cells (Tang, et al. Mol. Cancer Res. 2006 4: 371-377). VEGF secretion stimulated by the three different CD147-constructs (N- or C-terminal domain, or full-length ECD of CD147) of Example 1 were compared.

Figure 3:
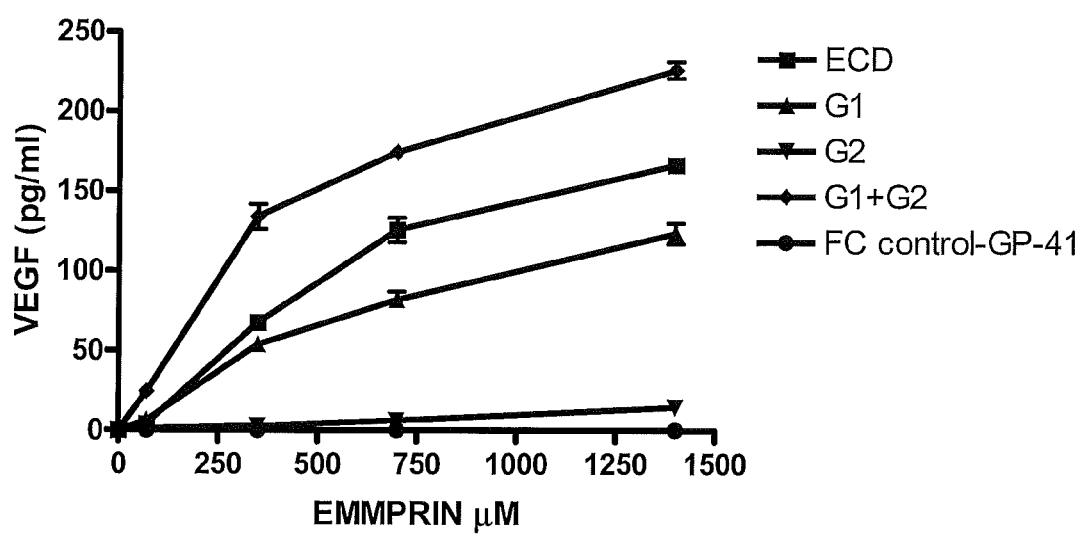
FIG. 3 is a graph showing the relative activity of CD147 ECD and subdomains (N-Domain is residues 19-117, C-Domain residues 95-204) as Fc-constructs in concentration-dependent stimulation VEGF production in NHLF.

Quantitation of the human VEGF concentration in the conditioned medium were performed using Quantikine ELISA kits from R&D Systems. The VEGF contained in 200 μl of standards or samples was captured by anti-VEGF antibodies immobilized on the bottom of assay wells detected by conjugated $2^{nd}$ antibody. ELISA data acquisition was performed using VersaMax Tunable MicoPlate Reader at 450 nm. Data were analyzed using Softmax Pro 3.1 software. The results (FIG. 3) indicate that the ECD construct is the most potent inducer of VEGF expression, with most of the activity residing within the N-domain. The C-domain contributes relatively little to VEGF induction.

CD147 Signaling

CD147 can stimulate production of MMP-1 and VEGF via the PI-3K-Akt signaling pathway. Akt phosphorylation in fibroblast cells was used as the basis of the measurement of CD147 signal transduction. Akt is a kinase also known as protein kinase B. Proteins phosphorylated by Akt generally promote cell survival. Recombinant CD147 can stimulate Akt phosphorylation in fibroblast cells (Tang et al., 2006, Mol. Cancer Res. 4 (2006), pp. 371-377). Experiments wherein the truncated ECD domains, N-domain or C-domain, where used instead of the full length ECD (ECD-FL) indicated that most of the activity was accounted for if the N-domain was used and relatively little signaling took place in the presence of the C-domain containing reagent protein only.

To further understand this signaling pathway and differentiate the role of different domain proteins, the effect of a specific Akt inhibitor, Akt V, on CD147-stimulated MMP-1 and VEGF production in NHLF cells was tested (FIG. 4). The results indicate that Akt V inhibits VEGF expression FIG. 4A, but not MMP-1 FIG. 4B, expression induced by CD147 domain proteins.

NF-kappa$_b$ is also reported to regulate VEGF expression and be a downstream target of the Akt signaling pathway. To test if NF-kb signaling is linked with the production of MMP and VEGF induced by CD147 domain proteins, NHLF cells were treated with the NF-kb inhibitor, Bay11-7082, after stimulation with different CD147 proteins (not shown) are similar to that for the Akt inhibitor in so far as Bay11-7082 inhibits VEGF expression but not MMP-1 expression induced by CD147 ECD and the N-domain but not the C-domain exhibit the majority of the activity VEGF inducing activity.

Example 3

Generation of Anti-CD147 Antibodies

Murine anti-human CD147 were generated by the hybridoma method of Kohler and Milstein. In addition, a surrogate antibody to murine CD147 was also generated.

Three 12-14 week old Balb/c mice were obtained from Charles River Laboratories. Two of the mice each received a combination of intradermal and intraperitoneal injections of 25 mg recombinant human CD147 $ECD_{25-205}$-Fc (R&D Systems) at 12.5 mg/site in 75 mL PBS emulsified in an equal amount of Freund's complete adjuvant on day 0. On Days 14, 28 and 51, they were injected with 25 mg ECD in 75 mL PBS emulsified in an equal amount of Freund's incomplete adjuvant. The third mouse received an initial injection of 25 mg of human ECD+0.33×105 U murine IFNa+0.33×$10^5$ U murine IFNb (Biosource) in 100 ml PBS administered subcutaneously (sc) at the base of the tail. On days 2 and 3, the mouse received additional injections of 0.33×$10^5$ U IFNa+0.33×$10^5$ U IFNb in 100 mL PBS administered sc at the base of the tail. Several weeks later, the mouse was boosted with 25 mg CD147 administered sc at the base of the tail. The mice were bled at various time-points throughout the immunization schedule. Blood collections were performed by retro-orbital puncture and serum was collected for titer determination by solid phase EIA. Once titer plateau was obtained, the mice received their final booster of 25 mg of ECD in PBS given intravenously (IV). Three days later the mice were euthanized by CO2 asphyxiation, and the spleens were aseptically removed and immersed in 10 mL cold PBS containing 100 U/mL penicillin, 100 mg/mL streptomycin, and 0.25 mg/mL amphotericin B (PBS/PSA). Lymphocytes were harvested by sterilely passing cells though a wire mesh screen immersed in cold PBS/PSA. The cells were washed once in cold PSA/PBS, counted using Trypan blue dye exclusion and resuspended in 10 mL PBS. The non-secreting mouse myeloma fusion partner cell line FO was maintained in log phase culture until fusion. The FO cells were washed in PBS, counted, and viability determined (>95%) via trypan blue dye exclusion prior to fusion. A total of three fusions were performed. Splenocytes were fused at a 1:1 ratio with FO cells. Briefly, splenocytes and myeloma cells were mixed together and pelleted and washed twice in 50 mL of PBS. The pellet was resuspended with 2 mL of fusing solution (5 ml PEG molecular weight 3000, 5 mL H2O (pH 7.0), 0.5 ml DMSO) at 37° C. over 1 minute. The cell/fusion mixture was then immersed in a 37° C. water bath for approximately 90 seconds with gentle agitation. The fusion reaction was stopped by adding 37° C. PBS in slow increments at 1 ml in the first 30 seconds, 3 ml in next 30 seconds, 16 ml in following 60 seconds. The fused cells were then centrifuged at 1000 rpm for 5 minutes. The cells were resuspended in fusion medium and plated at 200 mL/well in twenty 96-well flat bottom plates. The fusion plates were then placed in a humidified 37° C. incubator containing 6% $CO_2$ and left undisturbed for 7-10 days.

A neutralizing monoclonal antibody to murine CD147 was generated by immunizing rats with the extracellular domain of mouse CD147. Following immunizations and fusion, hybridomas were screened for binding to mouse CD147 and then assessed for in vitro activity. The antibody, designated C947, does not cross-react with human CD147, inhibited the expression of mouse CD147_induced MMP-1 production by NIH3T3 cells (mouse fibroblast) and MMP-2 in a co-culture of NIH3T3 & MISA (mouse tumor cell line) cells with no exogenous mouse CD147 added. V-region cloning of the C947 hybridoma resulted in single heavy and light chain sequences that, when expressed recombinantly, possessed the original activity of C947.

Example 4

Characterisation of Anti-CD147 Mabs

The hybridoma supernatants were screened for binding to CD147 in the solid phase (EIA) assay format. This screen yielded fifty-two positive clones.

A live cell-binding assay was used for further screening of the fifty-two clones. This screen yielded thirteen positive clones.

The thirteen positive clones were further tested in an MMP-1 assay. After screening by MMP-1 assay, 10 positive clones were identified.

Finally, the activity of the ten clones was characterized with a co-culture assay. This screen yielded seven positive clones from which mAbs were purified for further characterization and designated 2H3, 5F6, 2C8, 4D12, 4G1, 5A9 & 4A5.

Example 5

Bioactivity of Mabs

The seven mAbs identified by the screens described in Example 2 were analyzed for binding specificity and affinity within the extracellular domain of CD147. Data using proteins encoding either the N-domain (Asp19 to Asp117 of SEQ ID NO: 1) or the C-domain (Glu95 to Ser204) indicated that all seven bound specifically to the N-domain and not the C-domain.

The seven Mabs were rescreened for live cell binding against CD147-positive MDA-MB-231 breast carcinoma cells and to CD147-negative NHLF (FIG. 5). All seven antibodies recognized MDA-MB-231 cells that express native CD147 antigens on tumor cell surface. In contrast, none of these antibodies had any detectable binding to human fibroblast cells that are negative for CD147 expression.

The binding affinity of the mAbs estimated by solid phase binding assay. Four neutralizing antibodies, 2C8(mIgG1), 2H3(mIgG1), 5F6(mIgG1) and 4D12(mIgG1), exhibited the highest affinity binding to recombinant CD147 than RDI-CD147 of the seven mAbs tested.

Figure 6:
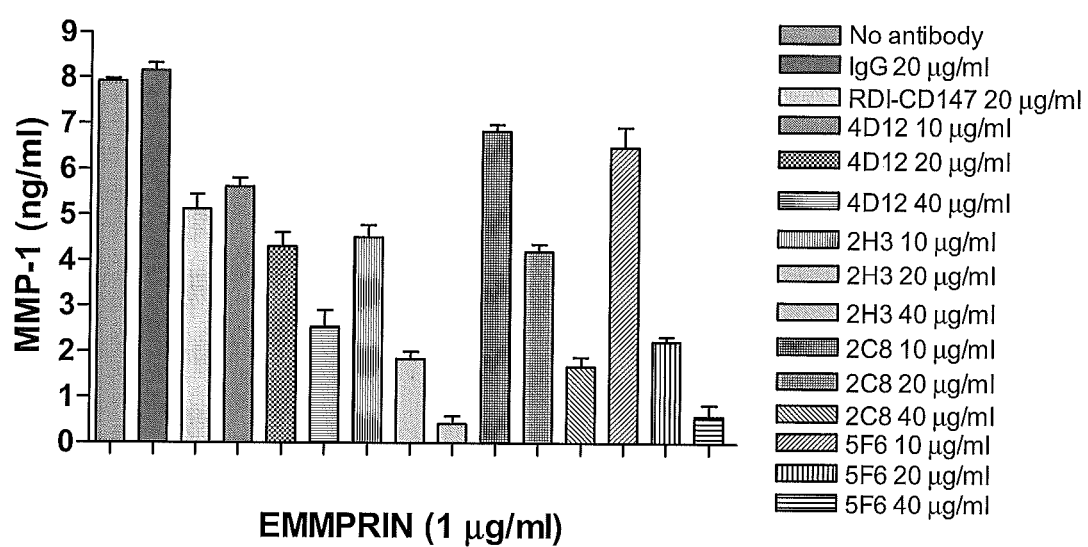
FIG. 6 is a graph showing the relative ability of selected purified murine antibodies (mIgG1) block CD147 (CD147) stimulated MMP-1 production in NHLF.

To assess the ability of the mAbs to block MMP-1 production, NHLF were treated with recombinant a ECD-Flag construct at 1 µg/ml. MMP-1 production in response to CD147 stimulation was determined using MMP-1 activity assay. All seven purified anti-CD147 antibodies were included in the assay to assess their inhibitory activity. Four mAbs showed significant inhibition of MMP-1 production. The 2H3 (mIgG1), 2C8(mIgG1), and 5F6(mIgG1) mAbs were the most potent, inhibiting MMP-1 production to minimal levels when used at 40 µg/ml (FIG. 6).

Figure 7:
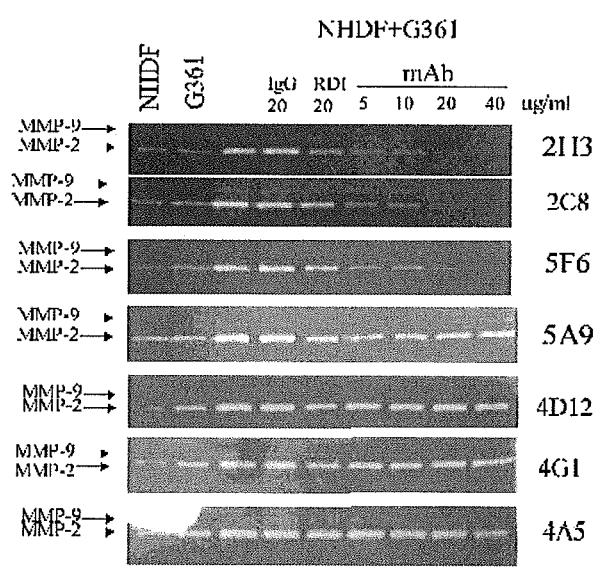
FIG. 7 shows zymograms demonstrating the relative ability of selected murine antibodies (mIgG1) to block MMP-2 and MMP-9 production in co-cultures of human tumor and human fibroblast cells.

The antibodies were screened for the ability to inhibit CD147-induced MMP-2 or MMP-9 production in co-culture. Three out of the seven mAbs 2H3(mIgG1), 2C8(mIgG1), 5F6(mIgG1)) screened in this assay inhibited MMP-2 and MMP-9 production in co-culture (FIG. 7). 4D12(mIgG1) did not exhibit substantial inhibitory activity in this assay. 5A9 (mIgG1) appeared to be inhibitory, but its inhibitory activity was not dose-dependent (FIG. 7).

Affinity for the CD147 ECD was also measured by surface plasmon resonance (Biacore). Kinetic studies were performed at 25° C. using a BIACORE 3000 (BIAcore, Inc.) surface plasmon resonance (SPR) instrument. Goat anti-mouse Fcγ specific antibody (Jackson Immunoresearch laboratories Prod #115-005-071) was covalently attached to carboxymethyl dextran coated gold surfaces (CM-5 Chip, Biacore). The carboxymethyl groups of dextran were activated with N-Ethyl-N'-(3-Dimethylaminopropyl) carbodiimide (EDC) and N-hydroxysuccinimide (NHS). The Ab was attached at pH 4.5 in 10 mM sodium acetate. Any remaining reactive sites on the surface were blocked by reaction with ethanolamine.

For kinetic binding measurements, anti-CD147 mAbs were captured using an anti-mouse Fcγ specific antibody at a flow rate of 30 µL/min. Ab capture was followed by injection of CD147-FL-ECD or the N- or C-domain fragments (as described in Example 1) at concentrations between 75 and 300 nM at 60 µL/min. Association data was collected for 2 min followed by 10 min of dissociation. The surface was regenerated with 15 µL of 100 mM H3PO4, followed by 15 µL of 50 mM NaOH at 30 µL/min. All samples were prepared in D-PBS containing 3 mM EDTA and 0.005% surfactant P20. Data reported is the difference in SPR signal between the flow cell containing the captured antibody and a reference cell without captured antibody. Additional instrumental contributions to the signal were removed by subtraction of the data from the blank injection from the reference-subtracted signal. Data were analyzed by fitting association and dissociation phases at all concentrations using the BIAevaluation software (BIAcore, Inc.).

The data indicated that three mAbs 2H3(mIgG1), 5F6 (mIgG1) and 2C8(mIgG1) have nM affinity to CD147 and binding to the N-domain but not the C-domain.

A summary of the activities of these mAbs are shown in the Table 1 (below) where the co-culture inhibition refer to the assay for MMP-2 and MMP-9 production.

TABLE 1

| Clone | C Code | Binding affinity (nM) to ECD | | | MMP-1 $IC_{50}$ (ug/ml) | Live cell binding (OD) | MMP2- and MMP-9 Inhibition |
|---|---|---|---|---|---|---|---|
| | | FL | N-term | C-term | | | |
| 2H3 | C1164A | 17 | 8 | No | ~10 | ~2.0 | Yes |
| 2C8 | C1170A | 5 | 0.43 | No | 20 | 0.6 | Yes |
| 4A5 | C1177A | 100 | | | | | No |
| 4D12 | C1165A | 9 | 0.95 | No | ~10-20 | 0.7 | No |
| 4G1 | C1179A | | | | | | No |
| 5A9 | C1166A | | | | | | No |
| 5F6 | C1171A | 4 | 0.46 | No | ~10-20 | 1.5 | Yes |

Based on clones 2H3, 4A5, and 5F6 having the highest binding affinity (lowest binding Kd) and specificity for the N-terminal domain of the ECD, these clones were chosen to be cloned and expressed in larger amounts for further studies.

Example 6

Cloning of Anti-CD147 Mabs

The V-region nucleic acid sequences for the heavy and light chains for 2H3, 2C8, 5F6 and 4A5 were cloned from the hybridomas. The amino acid sequences are shown below, with CDRs annotated.

For cloning of the murine antibody chains from hybridoma clones C1164A (2H3), C1170 (2C8), C1171A (5F6), C1171A (4A5) a total of RNA (3 μg, isolated using Trizol according to Invitrogen protocol) was used for 5' RACE with oligo dT priming reverse transcription (GeneRacer kit, Invitrogen). Each cDNA obtained was used as a template in two separate PCR reactions (1 μl per reaction) to amplify the heavy or light chain variable region of the antibody. To amplify the variable region of HC, the GeneRacer 5' Primer was used with the Rat HC1 (#641) Primer for PCR amplification. The Heavy chain PCR product was a single band of around 700 bp. Platinum TAQ DNA polymerase High Fidelity was used for PCR and the anneal temperature for the PCR amplification was 650 C (940 C for 30 sec, 650 c for 30 sec, 720 c for 1 min.). To amplify the variable region of LC, the GeneRacer 5' Primer was used with the Rat LC1 (#644) Primer, then followed by the nested PCR using GeneRacer 5' nested Primer and Rat LC2 (#645) primer. The PCR condition was as described as above, and the light chain PCR product yielded a band of approximately 600 bp. The 600 bp band was purified from the agarose gel as a LC PCR product. In order to obtain the V-region sequences, the PCR products were cloned into the pCR4-TOPO vector (TOPO TA Cloning Kit for Sequencing, Invitrogen). M13 Forward or Reverse oligos (30 ng) were used to prime the sequence reactions. For one antibody, 5F6, one HC and two LCs V-region sequences were identified from sequencing. The HC and LCs were cloned into various expression vectors, using the ligase-independent cloning method. PCR primers are defined below.

TABLE 2

PCR primers for amplifying and cloning CD147 Murine mAb V-regions

| Primer | Sequence | SEQ ID NO: |
|---|---|---|
| Rat HC-1 | 5'-TGGGCTACGYTGCAGGTGAC | 6 |
| Rat LC-1 | 5'-CTCATGCTGTACGTGCTGTC | 7 |
| Rat LC-2 | 5'-CTTGACATTGATGTCTTTGG | 8 |

The translation products of the cloned V-region for each antibody heavy and light chain are shown below.

```
2H3
2H3-Vk
                                        (SEQ ID NO: 9)
DIVMSQSPSS LAVSVGEKVT MSCKSSQSLL YNNNQKNYLA

WYQQKPGQSP KLLIYWASTR ESGVPDRFTG SGSGTDFTLT

ISSVKAEDLA VYYCQQYYSY PFTFGSGTKL EIK

2H3-VH
                                        (SEQ ID NO: 10)
QVQLQQSGAE LAKPGASVKL SCKASGYTFT SYWMHWVKQR

PGQGLEWIGY INPGSGYTKY NQTFKDKATL TADKSSSTAY

MQLSSLTYED SAVYYCARVE GYRTTRYFDV WGTGTTVTVS

S

4A5
4A5-Vk
                                        (SEQ ID NO: 11)
DIVMSQSPSS LAVSVGEKVT MSCKSSQSLL YSSNQKNYLA

WYQQKPGQSP KLLIYWASTR ESGVPDRFTG SGSGTDFTLT

ISSVKAEDLA VYYCQQYYSY PTFGAGTKLE LK

4A5-VH
                                        (SEQ ID NO: 12)
EVQLQQSGPE LVKPGASVKI SCKASGYTFT DYYMNWVKQS

HGKSLEWIGG INPNNGGTSY NQKFKGKATL TVDKSSSTAY

MELRSLTSED SAVYYCARND GYRGYAMDYW GQGTSVTVSS

5F6
5F6-Vk-2
                                        (SEQ ID NO: 13)
SIVMTQTPKF LLVSAGDRVT ITCKASQSVS NDVAWYQQKP

GQSPKLLIYY ASNRYTGVPD RFTGSGYGTD FTFTISTVQA

EDLAVYFCQQ DYSSPYTFGG GTKLEIK

5F6-VH
                                        (SEQ ID NO: 14)
EMKLEESGGG LVQPGGSMKL SCVASGFTFS NYWMNWVRQS

PEKGLEWVA QIRLKSYNYAT HYAESVKGRF TISRDDSKSS

VYLQMNNLRA EDTGIYYCTP DGSDYWGQGT TLTVSS

2C8
2C8-Vk
                                        (SEQ ID NO: 15)
MDMMVLAQFL AFLLLWFPGA RCDILMTQSP SSMSVSLGDT

VSITCHASQG ISSSIGWLQQ KPGKSFKGLI YHGTNLEDGV

PSRFTGSGSG ADYSLTISSL ESEDFADYYC VQYAQFPYTF

GGGTKLEIK

2C8-VH
                                        (SEQ ID NO: 16)
MDLRLSCAFI IVLLKGVQSE MKLEESGGGL VQPGGSMKLS

CVASGFTFSN YRMNWVRQSP EKGLEWVAQI RLKSYNYATH

YAESVKGRFT ISRDDSKSSV YLQMNNLRAE DTGIYYCTPD

GSDYWGQGTT LTVSS
```

Example 7

Bioactivity of Recombinant Mabs

The ability of the binding domains from the murine antibodies to block certain bioactivities of CD147 associated with pathologies such as neoplastic tissue growth and metastatic spread were evaluated using complete antibodies expressed as murine mAbs (mIgG1) or V-region chimera with either human IgG1 or murine IgG2a constant regions, which contribute antibody effector functions in in vivo assays. The methods of constructing such chimeras are well known in the art. In some assays, the commercially available CD147 neutralizing antibody, RDI-CD147, (R&D Systems) was used as a comparator.

Inhibition of CD147-Induced MMP-1 Release in Monocultured NHLF

The assay was conducted as described in Example 4. To determine the inhibitory activity of anti-CD147 antibodies, mAb 2H3(mIgG2a) and F6(hIgG1) were added into cell culture at 1, 5, 10, and 20 ug/ml after cells were stimulated with recombinant CD147 (ECD19-205-Fc construct) for 15 minutes. The data (Table 3) showed that CD147-stimulated MMP-1 production by fibroblast cells was inhibited by recombinant anti-CD147 mAb 2H3(mIgG2a) and 5F6 (hIgG1) in a dose-dependent manner.

TABLE 3

| Group | Conc. (µg/ml) | Mean MMP-1 (ng/ml) | Std Error of Mean |
|---|---|---|---|
| Control | 0 | 12.3 | 0.651 |
| IgG1 control | 10 | 12.3 | 0.887 |
| 2H3 (mIgG2a) | 1 | 10.5 | 0.255 |
| 2H3 (mIgG2a) | 5 | 6.86 | 0.549 |
| 2H3 (mIgG2a) | 10 | 3.87 | 0.452 |
| 2H3 (mIgG2a) | 20 | 1.71 | 0.244 |
| 5F6 (hIgG1) | 1 | 10.6 | 0.42 |
| 5F6 (hIgG1) | 5 | 7.24 | 0.639 |
| 5F6 (hIgG1) | 10 | 2.14 | 0.577 |
| 5F6 (hIgG1) | 20 | 1.49 | 0.35 |

Inhibition of MMP-2 Production in Co-Culture

Figure 8:
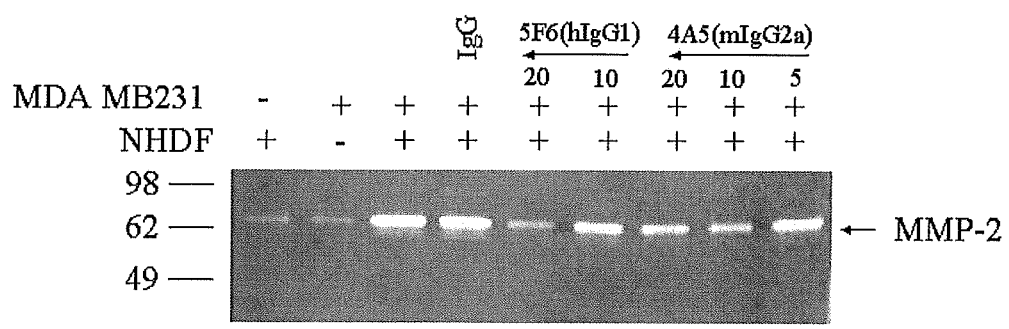
FIG. 8 is a zymogram showing MMP-2 release in co-cultures of human tumor and human fibroblast cells in attenuated by recombinant anti-CD147 antibodies 2H3(mIgG2a) and 5F6(hIgG1).

The assay was conducted as described in Example 4 using a co-culture assay of MDA-MB-231 and NHDF in the presence and absence of two recombinant anti-CD147 antibodies: 5F6(hIgG1) and 4A5(mIgG2a). Both antibodies inhibited the MMP-2 production by MDA-MB-231 and NHDF in a dose-dependent manner (FIG. 8).

Inhibition of VEGF Production

Figure 9:
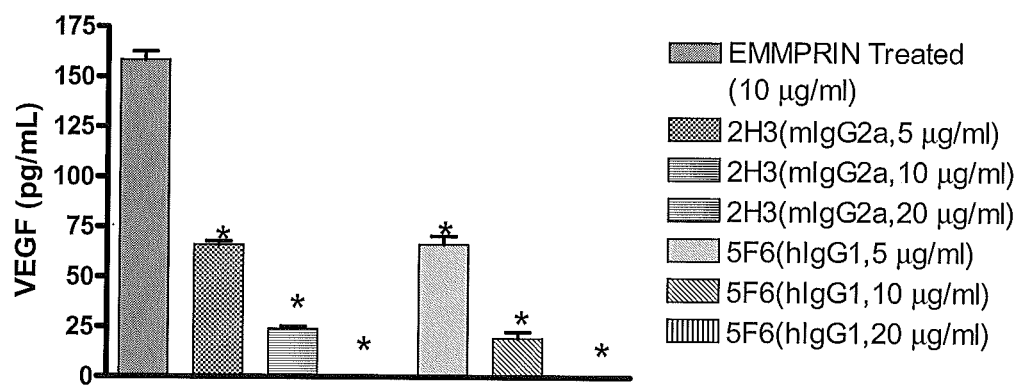
FIG. 9 is a bar graph showing that anti-CD147 antibodies 2H3(mIgG2a) and 5F6(hIgG1) inhibit CD147 induced VEGF from NHLF.

To determine the inhibitory activity of anti-CD147 antibodies, antibodies were added to NHLF cell culture and the cells were stimulated with recombinant CD147 for 15 minutes. Conditioned medium was collected at 48 hours. The data (FIG. 9) indicate that both 2H3(mIgG2a) and 5F6(hIgG1) mAbs were able to inhibit VEGF production by normal human lung fibroblasts (NHLF) stimulated with 10 µg/ml recombinant CD147 for 48 hours.

Since CD147 expression on tumor cells influenced VEGF expression in co-culture of tumor cells and fibroblasts, the ability of recombinant anti-CD147 mAbs, 2H3(mIgG2a) and 5F6(hIgG1), to suppress CD147-mediated tumor-stroma VEGF production was tested. This assay was performed as described in Example 4 with the following changes. Tested mAbs were added into the co-cultures. After 3 days, culturing medium was again replaced with 1.0 ml of serum-free DMEM medium and mAbs. Conditioned media were collected 2 days later for analysis of VEGF concentrations. The data showed that both recombinant anti-CD147 mAbs 2H3 (mIgG2a) and 5F6(hIgG1) at 20 µg/ml inhibited more than 40% of VEGF production in co-culture of tumor cells and fibroblast cells.

Example 8

In Vivo Activity

Inhibition of Angiogenesis

MATRIGEL™ is a solubilized basement membrane preparation extracted from the Engel-Holm-Swarm (EHS) mouse sarcoma, a tumor rich in extracellular matrix proteins. The major component is laminin, but MATRIGEL also contains trace amounts of fibroblast growth factor, TGF-beta, tissue plasminogen activator, and other growth factors that occur naturally in the EHS tumor. MATRIGEL is the basis for several types of tumor cell invasion assays and provides the necessary substrate for the study of angiogenesis. MATRIGEL forms a soft gel plug when injected subcutaneously into mice or rats and supports an intense vascular response when supplemented with angiogenic factors.

Experiment 1

The anti-angiogenic effects of anti-CD147 antibodies recombinant 2H3 and 5F6, 4D12 purified from hybridoma supernatant, and a rat anti-murine CD147 antibody (C947) were evaluated using a MATRIGEL plug assay. On day 1 of the study, 50 nude mice were randomized into 10 groups (n=5/group) as shown below. Mice were weighed and anesthetized with Ketamine/Xylazine (90/10 mg/kg, i.p.). The mice were injected in two sites with 0.5 ml of Matrigel (with 0.5 million cells/ml MATRIGEL) on each side. Test substances were injected i.p., on Days 1 and 4 at 10 mg/kg per therapeutic. On Day 1 the therapeutics were injected 3 hours prior to implanting the MATRIGEL plug as defined in Table 4 below. Anti-CD147 antibodies 2H3(mIgG2a), 5F6(hIgG1), 4D12(mIgG1), C947(rat IgG1) and cVam (and nonspecific mAbs used as a control) were diluted to appropriate concentrations enabling the administration of a total volume of 0.5 ml I.P. of each mAb per 20 gm of body weight. Where indicated, the agents were mixed together (1:1) prior to injection.

TABLE 4

| Group Number | Matrigel (M) contents | Treatment |
|---|---|---|
| 1 | M + DMEM | PBS |
| 2 | M + Panc-1 | PBS |
| 3 | M + Panc-1 | CVaM + PBS |
| 4 | M + Panc-1 | 2H3 (mIgG2a) + PBS |
| 5 | M + Panc-1 | 2H3 (mIgG2a) + C947 (rat IgG1) |
| 6 | M + Panc-1 | 5F6 (hIgG1) + PBS |
| 7 | M + Panc-1 | 5F6 (hIgG1) + C947 (rat IgG1) |
| 8 | M + Panc-1 | 4D12 (mIgG1) + PBS |
| 9 | M + Panc-1 | 4D12 (mIgG1) + C947 (rat IgG1) |

On day 8, all mice were euthanized by CO2 asphyxiation. Plugs were surgically removed and weighed in a blinded fashion. One plug/animal (right side) was assayed for hemoglobin content, which was used as an indirect index of the angiogenic response. The other plugs were processed for gross image analysis.

Figure 10:
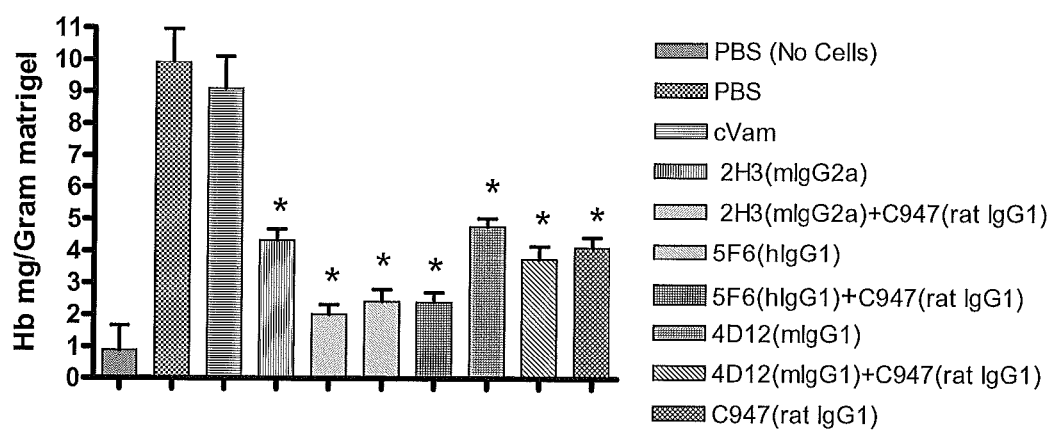
FIG. 10 is a bar graph showing the hemoglobin (Hb) content on Day 8 in Matrigel plugs implanted with PANC-1 (human pancreatic tumor cells) taken from nude mice after receiving 10 mg/kg mAbs injected i.p., on Days 1 and 4.

The data (FIG. 10) demonstrated that recombinant anti-CD147 mAbs, 2H3(mIgG2a) and 5F6(hIgG1), either alone or in combination with anti-murine CD147 (c947) mAb, significantly inhibited angiogenesis in vivo.

Experiment 2

To evaluate and compare the inhibitory effects of anti-CD147 mAbs (4A5, 5F6) on angiogenesis stimulated by CD147 derived from PANC-1 cancer cells embedded in MATRIGEL plugs in female SCID mice.

MATRIGEL was purchased from Becton Dickinson, Inc. and used at 11.1 mg/ml. PANC-1 human pancreatic tumor cells were supplied in serum-free DMEM.

The antibodies were prepared with murine constant regions so that both an effector function positive isotype (E+mIgG2a) and an effector negative isotype (E-mIgG1) were represented for each pair of variable domains.

Forty-two female SCID mice (6 weeks old) obtained from Charles Rivers (Raleigh, N.C.) were group housed (7/cage) in filter topped plastic cages and supplied, free choice, with autoclaved food and water. On day 0 of the study, 42 SCID mice were shaved and randomized into 6 groups (n=7/group). On Day 1 test substances were injected i.p., at 0.2 mL/20 g body weight (10 mg/kg), 3 hours prior to implanting the matrigel plug, and then again on day 5.

Mice were weighed and anesthetized with Ketamine/Xylazine (90/10 mg/kg, i.p.). Except for one group, the mice were injected in two sites with 0.5 ml of MATRIGEL.

On day 9, all mice were euthanized and the plugs were surgically removed and weighed in a blinded fashion. The plugs were assayed for hemoglobin content, as an indirect index of the angiogenic response.

Analysis of the hemoglobin levels was performed on the average of two measurements from each mouse.

TABLE 5

| Group | n | Geometric Mean | Model Based Std. Error | 95% Confidence Interval (Lower, Upper) | |
|---|---|---|---|---|---|
| PBS (No Cells) | 7 | 0.343 | 0.206 | 0.102 | 1.161 |
| PBS (with Panc-1 cells) | 7 | 25.099 | 15.058 | 7.426 | 84.839 |
| E − 4A5 (7709) | 8 | 19.333 | 10.849 | 6.188 | 60.405 |
| E + 4A5 (9633) | 7 | 0.781 | 0.469 | 0.231 | 2.641 |
| E − 5F6 (8261) | 8 | 5.481 | 3.076 | 1.754 | 17.124 |
| E + 5F6 (7603) | 4 | 0.261 | 0.207 | 0.052 | 1.308 |

The data table above (Table 5) shows the estimated mean and standard error as well as the confidence interval for hemoglobin by group. The plugs containing untreated MATRIGEL with Panc-1 cells had the highest hemoglobin levels of 25.10±15.06 mg/gm. The E+5F6 (CNTO 7603) group has the lowest hemoglobin levels of 0.26±0.21 mg/gm.

The Global F-test P-value is <0.001. There is evidence of significant statistical differences amongst the groups. All of the pairwise comparisons were performed between the groups. The plug without cells, PBS-treated group was significantly smaller than the untreated (PBS) group with Panc-1 cells, the E-425 (CNTO7709) group, and the E-5F6 (CNTO 8261) group (p-values of <0.001, <0.001, and 0.002, respectively). A difference was not detected statistically between the PBS-treated plugs without cells group and the E+ groups, E+4A5 (CNTO8261) and E+5F6 (CNTO7603).

A significance decrease in hemoglobin levels was detected when the groups of from MATRIGEL with cells treated with E+Mabs were compared to PBS with cells. E+4A5 (CNTO 9633) was 97%±3% smaller than PBS with MATRIGEL with cells (p-value <0.001), and E+5F6 (CNTO7603) was 99%±1% smaller than PBS with MATRIGEL with cells (p-value <0.001). The difference in Hemoglobin between the PBS with MATRIGEL with cells and the E-5F6 (CNTO8261) treatment just missed statistical significance (p-value=0.072). Only a 23%±66% difference (p-value=0.753) was detected between the PBS with MATRIGEL with cells and the E-4A5 (CNTO7709) groups.

In comparing the two 4A5 groups, the E+ (CNTO9633) is significantly smaller than the E− (CNTO7709) hemoglobin level. The estimated difference is 99%±3% (p-value <0.001). In comparing the two 5F6 groups, the E+(CNTO7603) is significantly smaller than the E− (CNTO8261) hemoglobin level. The estimated difference is 95%±5% (p-value=0.004).

No significant difference was detected between the two E+ (CNTO9633 vs. CNTO7603) groups or between the two E− groups (CNTO7709 vs. CNTO8261). In comparing the two 4A5 groups, the E+4A5 is significantly lower than the E-4A5 hemoglobin level. In comparing the 5F6 groups, the E+5F6 is significantly lower than the E-5F6 hemoglobin level. No significant difference was detected between the E+ groups or between the two E− groups. The data indicated E+, not E−, 5F6 and 4A5 inhibit tumor angiogenesis in Panc-1 matrigel plug model.

Inhibition of Tumor Growth in an MDA-MB-231 Orthotopic Tumor Xenograft Model

To determine anticancer effects of anti-CD147 function-blocking antibodies on tumor progression, SCID Beige Mice implanted with MDA-MB-231 human breast carcinoma cells were treated with E+4A5(MuIgG2a) or E+5F6(MuIgG2a).

On day 0, 40 female SCID beige mice were anesthetized with Ketamine/Xylazine (90/10 mg/kg, ip). The animals were implanted orthotopically in the right axillary second or third mammary fat pad with 0.05 ml ($2.5 \times 10^6$ cells) of the MDA-MB-231 cell suspension.

All animals were weighed at the start of the study and once a week throughout the course of the study. When the mean tumor volume was between 60-70 mm3, the animals were stratified to one of three groups with 8 animals per group: PBS only, E+5A6 or E+4A5 at 1 mg/Kg administered twice a week for the remainder of the study (50 days total). Tumor growth was measured weekly with calipers in two dimensions (length and width) in millimeters (mm), and the tumor volume (mm3) was calculated based on the formula [length×width×width]/2.

At the end of the study, mice were euthanized by $CO_2$ asphyxiation. Primary tumors were excised and weighed on a digital balance. Lungs were removed, weighed and lung metastases were perfused with India Ink and placed into Fekete's solution for metastasis enumeration in a blinded fashion.

Results

For the tumor volume, a repeated measures model was fit to the data assuming a first-order autocorrelation covariance structure. Natural splines were used to model the curvature of trends in the time profiles. Pairwise comparisons amongst the groups were made at each of the time points. Calculations were performed using the R software environment.

Both classical, and resistant and robust ANOVA were applied to the lung metastasis counts and the results from the two methods were compared. The conclusions from both analyses were the same, however, the assumptions of equal variance among the groups and sampling from a normal distribution are more reasonably met for the resistant and robust analysis.

Figure 11:
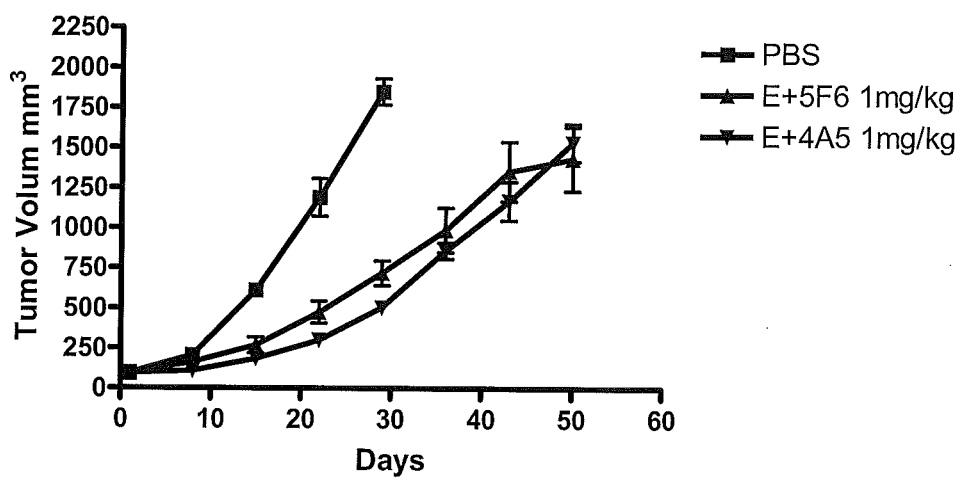
FIG. 11 shows tumor volume change over time in mice receiving recombinant anti-CD147 antibodies, 2H3 (mIgG2a) and 5F6(hIgG1), which are effector positive isotypes (E+) or PBS.

Primary tumor growth curves are shown (FIG. 11). Beginning on Day 7 after treatment initiation, tumor growth in the E+4A5(muIgG2a) and the E+5F6(muIgG2a) groups was significantly inhibited compared to the PBS control group (p<0.001 for all pair-wise comparisons; see Appendix 1 for details of the statistics). This difference increases as the number of days increases. Treatment with E+4A5(muIgG2a) resulted in significantly smaller tumor volumes than E+5F6 (muIgG2a) from days 7 to 28.

Both E+5F6(muIgG2a) and E+4A5(muIgG2a) significantly increase the average time (i.e. delay) until in time for tumor volume to reach 1500 $mm^3$, relative to PBS group (both p-values=<0.001). E+4A5(muIgG2a) also significantly increased (18%±6%; p-value=0.004) the number of days until the 1500 mm3 threshold was reached compared to E+5F6(muIgG2a).

This data indicates that E+ anti-EMMPRIN antibodies are capable of inhibiting primary tumor growth at this dose.

All of the lungs from the mice in the PBS group contained numerous lung metastases (Mean±Std Dev.=122±14.0) while the number of metastatic lesions in the lungs of E+4A5 (muIgG2a) and E+5F6(muIgG2a) antibody-treated groups was significantly reduced (17.8±12.1 and 17.5±13.7, respectively) and the overall P value was <0.001. No significant differences were detected for the number of lung metastases between E+5F6(muIgG2a) and E+4A5(muIgG2a) treatments (p-value=0.970). In both E+5F6(muIgG2a) and E+4A5(muIgG2a)-treated groups, there were mice apparently free of lung metastases (1 mouse in each group). These results suggest that neutralization of EMMPRIN may inhibit the formation or delay the growth of lung metastases from primary MDA-MB-231 orthotopic tumors.

Example 9

Epitope Mapping

The binding sites for the 4A5 and 5F6 mAbs on human CD147 were defined by a combination of an antibody competitive binding assay, H/D Exchange and single point mutagenesis and interpreted in the context of published and internally generated structures of human EMMPRIN fragments. The results show that the antibodies bind to similar epitopes in the extracellular domain of CD147.

For H/D exchange, recombinant CD147 ECD N-domain (Asp 19 to Asn 117-hexahis) was incubated in a deuterated water solution for predetermined times resulting in deuterium incorporation at exchangeable hydrogen atoms. The deuterated EMMPRIN was captured on a column containing immobilized 4A5 Fab (expressed from *E. coli* with C-terminal His-tag) or 5F6 mAb and then washed with aqueous buffer. The back-exchanged CD147 domain protein was eluted from the column and localization of deuterium containing fragments was determined by protease digestion and mass spec analysis. Regions bound to the antibody were inferred to be those sites relatively protected from exchange and thus contain a higher fraction of deuterium than CD147 not complexed with antibody. H/D exchange perturbation of Asp19 to Asn117-hexahis in shown in FIG. 12.

The H/D exchange data for 4A5 implicate two segments (Leu90-Asn98>Asp65-Phe74). However, these two segments exist on two opposing sides of the three-dimensional conformation of the N-domain reagent, and therefore it is improbable that the antibody bound both. It was observed that the residues 90-98 associate to form dimeric structures. The H/D difference observed between antibodies in this region likely results from structural (allosteric) stabilization due to 4A5 binding. Thus, Leu90-Asn98 is ruled out and Asp65-Phe74 is the likely epitope region. H/D exchange studies with the 5F6 antibody binding indicate binding to the Asp65-Phe74 peptide and possibly to the region Val30 to Thr40. These two segments are structurally close and thus, it is possible for both to be part of the epitope.

Single point mutagenesis of the N-terminal domain of human CD147 was carried out as a second independent method for mapping the epitope of the 4A5 antibody using a bifunctional hybrid protein (BHP) display technology from Progenosis, Liege, Belgium (Chevigne et al. 2007. J Immunol Methods. 30: 81-93). Three single point mutants, D45, G69 and Q70, substantially reduced binding to 4A5 mAb. Two of these residues, G69 and Q70, lie within the Asp65-Phe74 segment identified by H/D exchange. The third residue, D45 lies in a flexible loop that is adjacent to 69GQ70. It suggested similarity in how each of the binding regions engage the target CD147 protein and that the epitope is present in the peptide, $_{65}$DALPGQKTEF$_{74}$ (SEQ ID NO.: 1) but that the region, $_{30}$VEDLGSKILLT$_{40}$ (SEQ ID NO.: 1), may also contribute to 5F6 binding epitope.

Figure 13:
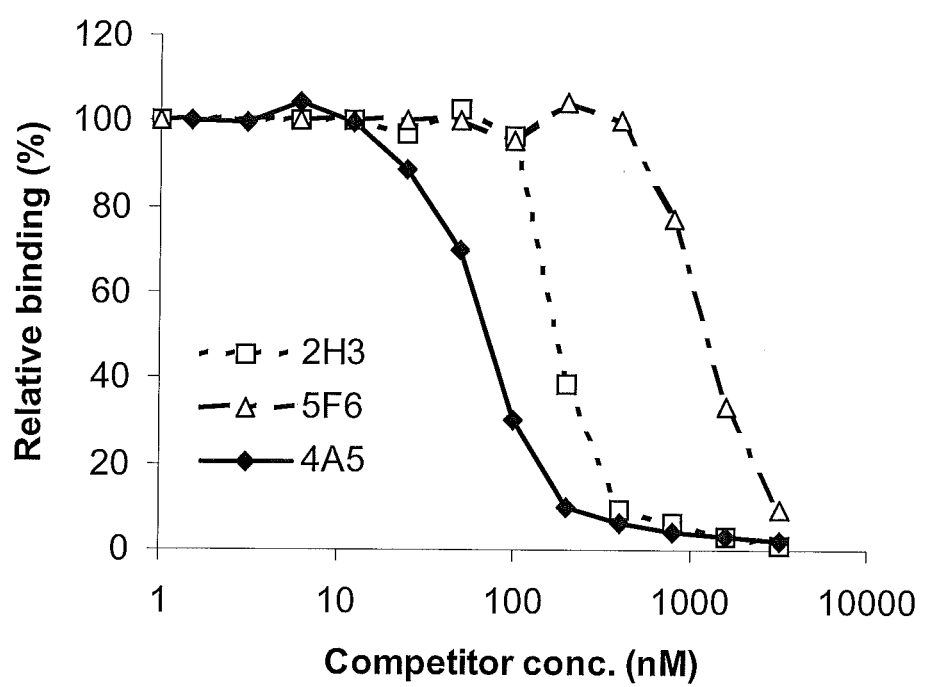
FIG. 13 is a graph showing competitive binding assays of 2H3 mAbs in competition with 4A5 or 5F6 for binding of the Asp19-Glu 192-Fc construct in an ELISA format.

Competition ELISA on microtiter plates coated with CD147 Asp19-Asn117-Fc fusion protein were carried out to evaluate the binding specificity for 2H3, 4A4 and 5F6 mAbs. Labeled 2H3 mAb was pre-incubated at room temperature for 30 minutes with different concentration mAbs. These mixtures were then added to the antigen-coated microwells. Following incubation at 37° C. for 2 hours, microtiter plates were washed thoroughly, and bound 2H3 was detected. The results indicate that both 4A5 and 5F6 compete with 2H3 mA (FIG. 13). The data suggested that 2C8 competes very successfully against both 2H3 and 5F6 (IC$_{50}$~30 nM) but that 2H3 and 5F6 do not compete well against each other (IC$_{50}$~1 μM). These data indicate that 2H3 and 5F6 have different epitopes and both are in close proximity or overlap with the 2C8 binding site.

In total, these results position the epitope for 4A5 in the region Asp65-Phe 74 and the loop region (40-50) centered near Asp45. The binding site for the 5F6 mAb also maps to Asp65-Phe74 together with Val30-Thr40.

What is claimed:

1. An isolated anti-CD147 antibody having Hc-CDR1, Hc-CDR2 and Hc-CDR3 amino acid sequences shown in SEQ ID NO: 10 and Lc-CDR1 Lc-CDR2, and Lc-CDR3 amino acid sequences shown in SEQ ID NO: 9.

2. An isolated anti-CD147 antibody having Hc-CDR1, Hc-CDR2 and Hc-CDR3 amino acid sequences shown in SEQ ID NO: 12 and Lc-CDR1 Lc-CDR2, and Lc-CDR3 amino acid sequences shown in SEQ ID NO: 11.

3. An isolated anti-CD147 antibody having Hc-CDR1, Hc-CDR2 and Hc-CDR3 amino acid sequences shown in SEQ ID NO: 14 and Lc-CDR1 Lc-CDR2, and Lc-CDR3 amino acid sequences shown in SEQ ID NO: 13.

4. An isolated anti-CD147 antibody having Hc-CDR1, Hc-CDR2 and Hc-CDR3 amino acid sequences shown in SEQ ID NO: 16 and Lc-CDR1 Lc-CDR2, and Lc-CDR3 amino acid sequences shown in SEQ ID NO: 15.

5. A humanized antibody comprising a humanized heavy chain and humanized light chain, wherein:
(a) the humanized heavy chain variable region comprises three complementarity determining regions (CDRS) from the mouse 4A5 heavy chain (SEQ ID NO: 12) and a framework from a human acceptor antibody heavy chain; and
(b) the humanized light chain variable region comprises three complementarity determining regions from the mouse 4A5 light chain (SEQ ID NO: 11) and a framework from a human acceptor antibody light chain; and
(c) wherein the humanized antibody specifically binds to a CD147 antigen on the surface of MDA-MB-231 cells.

* * * * *

SEQUENCE LISTING

<160> NUMBER OF SEQ ID NOS: 16

<210> SEQ ID NO 1
<211> LENGTH: 269
<212> TYPE: PRT
<213> ORGANISM: Homo sapiens

<400> SEQUENCE: 1

Met Ala Ala Ala Leu Phe Val Leu Leu Gly Phe Ala Leu Leu Gly Thr
1               5                   10                  15

His Gly Ala Ser Gly Ala Ala Gly Thr Val Phe Thr Thr Val Glu Asp
            20                  25                  30

Leu Gly Ser Lys Ile Leu Leu Thr Cys Ser Leu Asn Asp Ser Ala Thr
        35                  40                  45

Glu Val Thr Gly His Arg Trp Leu Lys Gly Gly Val Val Leu Lys Glu
    50                  55                  60

Asp Ala Leu Pro Gly Gln Lys Thr Glu Phe Lys Val Asp Ser Asp Asp
65                  70                  75                  80

Gln Trp Gly Glu Tyr Ser Cys Val Phe Leu Pro Glu Pro Met Gly Thr
                85                  90                  95

Ala Asn Ile Gln Leu His Gly Pro Pro Arg Val Lys Ala Val Lys Ser
            100                 105                 110

Ser Glu His Ile Asn Glu Gly Glu Thr Ala Met Leu Val Cys Lys Ser
        115                 120                 125

Glu Ser Val Pro Pro Val Thr Asp Trp Ala Trp Tyr Lys Ile Thr Asp

```
                    130                 135                 140
Ser Glu Asp Lys Ala Leu Met Asn Gly Ser Glu Ser Arg Phe Phe Val
145                 150                 155                 160

Ser Ser Ser Gln Gly Arg Ser Glu Leu His Ile Glu Asn Leu Asn Met
                165                 170                 175

Glu Ala Asp Pro Gly Gln Tyr Arg Cys Asn Gly Thr Ser Ser Lys Gly
                180                 185                 190

Ser Asp Gln Ala Ile Ile Thr Leu Arg Val Arg Ser His Leu Ala Ala
                195                 200                 205

Leu Trp Pro Phe Leu Gly Ile Val Ala Glu Val Leu Val Leu Val Thr
                210                 215                 220

Ile Ile Phe Ile Tyr Glu Lys Arg Arg Lys Pro Glu Asp Val Leu Asp
225                 230                 235                 240

Asp Asp Asp Ala Gly Ser Ala Pro Leu Lys Ser Ser Gly Gln His Gln
                245                 250                 255

Asn Asp Lys Gly Lys Asn Val Arg Gln Arg Asn Ser Ser
                260                 265

<210> SEQ ID NO 2
<211> LENGTH: 24
<212> TYPE: DNA
<213> ORGANISM: Homo sapiens

<400> SEQUENCE: 2
tcgaggtacc gccaccatgg cggc                                          24

<210> SEQ ID NO 3
<211> LENGTH: 30
<212> TYPE: DNA
<213> ORGANISM: Homo sapiens

<400> SEQUENCE: 3
tgcagcggcc gccgttgatg tgttctgacg                                    30

<210> SEQ ID NO 4
<211> LENGTH: 24
<212> TYPE: DNA
<213> ORGANISM: Homo sapiens

<400> SEQUENCE: 4
caagagggat ccgccggcac ggcc                                          24

<210> SEQ ID NO 5
<211> LENGTH: 23
<212> TYPE: DNA
<213> ORGANISM: Homo sapiens

<400> SEQUENCE: 5
tgcagcggcc gctgcgcacg cgg                                           23

<210> SEQ ID NO 6
<211> LENGTH: 20
<212> TYPE: DNA
<213> ORGANISM: Rattus rattus
<220> FEATURE:
<221> NAME/KEY: misc_feature
<222> LOCATION: (10)..(10)
<223> OTHER INFORMATION: Primer is a mixture where 10 may be C or T

<400> SEQUENCE: 6
tgggctacgy tgcaggtgac                                               20
```

<210> SEQ ID NO 7
<211> LENGTH: 20
<212> TYPE: DNA
<213> ORGANISM: Rattus rattus

<400> SEQUENCE: 7
ctcatgctgt acgtgctgtc                                          20

<210> SEQ ID NO 8
<211> LENGTH: 20
<212> TYPE: DNA
<213> ORGANISM: Rattus rattus

<400> SEQUENCE: 8
cttgacattg atgtctttgg                                          20

<210> SEQ ID NO 9
<211> LENGTH: 113
<212> TYPE: PRT
<213> ORGANISM: Mus musculus

<400> SEQUENCE: 9

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Asn
            20                  25                  30

Asn Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Phe Thr Phe Gly Ser Gly Thr Lys Leu Glu Ile
            100                 105                 110

Lys

<210> SEQ ID NO 10
<211> LENGTH: 121
<212> TYPE: PRT
<213> ORGANISM: Mus spp.

<400> SEQUENCE: 10

Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Gly Ser Gly Tyr Thr Lys Tyr Asn Gln Thr Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Tyr Glu Asp Ser Ala Val Tyr Tyr Cys
                85                  90                  95

Ala Arg Val Glu Gly Tyr Arg Thr Ala Arg Tyr Phe Asp Val Trp Gly
            100                 105                 110

Thr Gly Thr Thr Val Thr Val Ser Ser
        115                 120

<210> SEQ ID NO 11
<211> LENGTH: 112
<212> TYPE: PRT
<213> ORGANISM: Mus spp.

<400> SEQUENCE: 11

Asp Ile Val Met Ser Gln Ser Pro Ser Ser Leu Ala Val Ser Val Gly
1               5                   10                  15

Glu Lys Val Thr Met Ser Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Thr Phe Gly Ala Gly Thr Lys Leu Glu Leu Lys
            100                 105                 110

<210> SEQ ID NO 12
<211> LENGTH: 120
<212> TYPE: PRT
<213> ORGANISM: Mus spp.

<400> SEQUENCE: 12

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asn Asp Gly Tyr Arg Gly Tyr Ala Met Asp Tyr Trp Gly Gln
            100                 105                 110

Gly Thr Ser Val Thr Val Ser Ser
        115                 120

<210> SEQ ID NO 13
<211> LENGTH: 107
<212> TYPE: PRT
<213> ORGANISM: Mus spp.

<400> SEQUENCE: 13

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

```
Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105

<210> SEQ ID NO 14
<211> LENGTH: 116
<212> TYPE: PRT
<213> ORGANISM: Mus spp.

<400> SEQUENCE: 14

Glu Met Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
                20                  25                  30

Trp Met Asn Trp Val Arg Gln Ser Pro Glu Lys Gly Leu Glu Trp Val
            35                  40                  45

Ala Gln Ile Arg Leu Lys Ser Tyr Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Pro Asp Gly Ser Asp Tyr Trp Gly Gln Gly Thr Thr Leu
            100                 105                 110

Thr Val Ser Ser
            115

<210> SEQ ID NO 15
<211> LENGTH: 107
<212> TYPE: PRT
<213> ORGANISM: Mus musculus
<220> FEATURE:
<221> NAME/KEY: BINDING
<222> LOCATION: (27)..(32)
<223> OTHER INFORMATION: CDR1
<220> FEATURE:
<221> NAME/KEY: BINDING
<222> LOCATION: (50)..(52)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 15

Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Ser
                20                  25                  30

Ile Gly Trp Leu Gln Gln Lys Pro Gly Lys Ser Phe Lys Gly Leu Ile
            35                  40                  45

Tyr His Gly Thr Asn Leu Glu Asp Gly Val Pro Ser Arg Phe Thr Gly
    50                  55                  60

Ser Gly Ser Gly Ala Asp Tyr Ser Leu Thr Ile Ser Ser Leu Glu Ser
65                  70                  75                  80
```

-continued

```
Glu Asp Phe Ala Asp Tyr Tyr Cys Val Gln Tyr Ala Gln Phe Pro Tyr
                85                  90                  95

Thr Phe Gly Gly Gly Thr Lys Leu Glu Ile Lys
            100                 105

<210> SEQ ID NO 16
<211> LENGTH: 116
<212> TYPE: PRT
<213> ORGANISM: Mus musculus
<220> FEATURE:
<221> NAME/KEY: BINDING
<222> LOCATION: (26)..(33)
<223> OTHER INFORMATION: CDR1
<220> FEATURE:
<221> NAME/KEY: BINDING
<222> LOCATION: (51)..(60)
<223> OTHER INFORMATION: CDR2
<220> FEATURE:
<221> NAME/KEY: BINDING
<222> LOCATION: (99)..(105)
<223> OTHER INFORMATION: CDR3

<400> SEQUENCE: 16

Glu Met Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
                20                  25                  30

Arg Met Asn Trp Val Arg Gln Ser Pro Glu Lys Gly Leu Glu Trp Val
            35                  40                  45

Ala Gln Ile Arg Leu Lys Ser Tyr Asn Tyr Ala Thr His Tyr Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Pro Asp Gly Ser Asp Tyr Trp Gly Gln Gly Thr Thr Leu
            100                 105                 110

Thr Val Ser Ser
            115
```